US012677707B2

(12) United States Patent
Wu et al.

(10) Patent No.: US 12,677,707 B2
(45) Date of Patent: Jul. 7, 2026

(54) BIO SENSING DEVICE

(71) Applicant: InnoLux Corporation, Miao-Li County (TW)

(72) Inventors: Yuan-Lin Wu, Miao-Li County (TW); Chandra Lius, Miao-Li County (TW); Tsung-Han Tsai, Miao-Li County (TW); Kuan-Feng Lee, Miao-Li County (TW)

(73) Assignee: InnoLux Corporation, Miao-Li County (TW)

( * ) Notice: Subject to any disclaimer, the term of this patent is extended or adjusted under 35 U.S.C. 154(b) by 435 days.

(21) Appl. No.: 18/244,311

(22) Filed: Sep. 11, 2023

(65) Prior Publication Data

US 2024/0120326 A1 Apr. 11, 2024

(30) Foreign Application Priority Data

Oct. 9, 2022 (CN) .......................... 202211227178.0

(51) Int. Cl.
| | |
|---|---|
| *H10W 90/00* | (2026.01) |
| *A61B 5/00* | (2006.01) |
| *H10K 39/00* | (2026.01) |
| *H10K 59/60* | (2023.01) |
| *H10K 77/10* | (2023.01) |

(52) U.S. Cl.
CPC .......... *H10W 90/00* (2026.01); *H10K 39/601* (2023.02); *H10K 59/60* (2023.02); *H10K 77/111* (2023.02); *A61B 5/0059* (2013.01)

(58) Field of Classification Search
CPC .... H01L 25/167; H10K 39/601; H10K 59/60; H10K 77/111; H10K 39/34; A61B 5/0059; A61B 2562/0233; A61B 2562/046; A61B 2562/146; A61B 2562/164; A61B 5/1455; A61B 5/14556
See application file for complete search history.

(56) References Cited

U.S. PATENT DOCUMENTS

| | | | |
|---|---|---|---|
| 2016/0035940 A1* | 2/2016 | Fujita ................. | G06V 40/1324 |
| | | | 438/29 |
| 2021/0298672 A1 | 9/2021 | Lee | |
| 2022/0015641 A1* | 1/2022 | Lee ...................... | A61B 5/0075 |
| 2022/0042965 A1 | 2/2022 | Kang | |
| 2022/0117557 A1* | 4/2022 | Hsu ...................... | A61B 5/0261 |
| 2023/0200654 A1* | 6/2023 | Wu ...................... | H05K 1/0296 |
| 2023/0207581 A1* | 6/2023 | Shen ...................... | H10F 55/20 |

FOREIGN PATENT DOCUMENTS

TW M575531 U 3/2019

OTHER PUBLICATIONS

PET Transmittance downloaded from URL< https://endurancelasers.com/absorption-wavelength-spectrum-for-different-materials/> on Nov. 4, 2025. (Year: 2025).*

* cited by examiner

*Primary Examiner* — J. E. Schoenholtz
(74) *Attorney, Agent, or Firm* — Winston Hsu

(57) ABSTRACT

Disclosed is a bio sensing device including a medium layer, a light emitting element and an optical sensor. The light emitting element is configured to emit a light toward a user's skin layer, in which the light passes through the medium layer and has a maximum intensity in a first wavelength. The optical sensor is configured to receive a reflected part of the light from the user's skin layer, in which the reflected part of the light passes through the medium layer, and the medium layer has a first transmittance greater than 60% with respect to the first wavelength.

18 Claims, 15 Drawing Sheets

BIO SENSING DEVICE

BACKGROUND OF THE DISCLOSURE

1. Field of the Disclosure

The present disclosure relates to a bio sensing device, and particularly to a bio sensing device having a medium layer for a bio skin layer.

2. Description of the Prior Art

In conventional bio sensing devices, sensors are formed on a rigid substrate, such that the bio sensing device is not easy to be shaped with appearance of a user's bio feature and is not easy to be attached to a biological skin of the user, which causes the user to feel uncomfortable when using it and affects detection accuracy of the sensors. For this reason, the bio sensing device cannot meet the demands of the users. Also, the conventional bio sensing device is not easy to be stretched, so that elements therein are easily damaged during attaching the bio sensing device to the bio feature or removing the bio sensing device from the bio feature. Accordingly, the conventional bio sensing device is unable to meet requirements of repeated use. Therefore, providing a novel bio sensing device to improve above issues is an objective in this art.

SUMMARY OF THE DISCLOSURE

It is an objective of the present disclosure to provide a bio sensing device.

According to an embodiment of the present disclosure, a bio sensing device is provided and includes a medium layer, a light emitting element and an optical sensor. The light emitting element is configured to emit a light toward a user's skin layer, in which the light passes through the medium layer and has a maximum intensity in a first wavelength. The optical sensor is configured to receive a reflected part of the light from the user's skin layer, in which the reflected part of the light passes through the medium layer, and the medium layer has a first transmittance greater than 60% with respect to the first wavelength.

These and other objectives of the present disclosure will no doubt become obvious to those of ordinary skill in the art after reading the following detailed description of the embodiment that is illustrated in the various figures and drawings.

DETAILED DESCRIPTION

Figure 1:
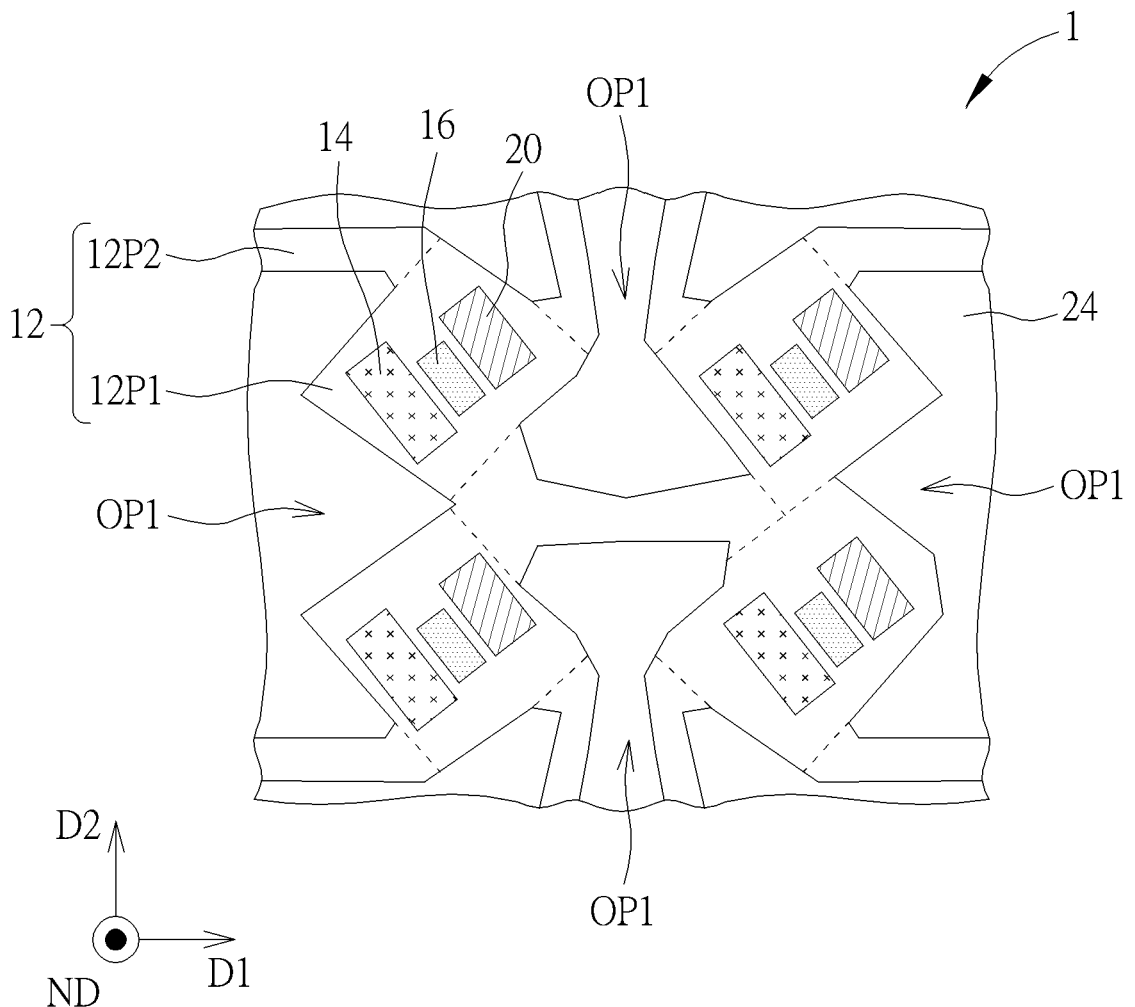
FIG. 1 schematically illustrates a top view of a bio sensing device placed on a skin layer of a user according to a first embodiment of the present disclosure.

The contents of the present disclosure will be described in detail with reference to specific embodiments and drawings. It is noted that, for purposes of illustrative clarity and being easily understood by the readers, the following drawings may be simplified schematic diagrams, and elements therein may not be drawn to scale. The numbers and sizes of the elements in the drawings are just illustrative and are not intended to limit the scope of the present disclosure.

Certain terms are used throughout the specification and the appended claims of the present disclosure to refer to specific elements. Those skilled in the art should understand that electronic equipment manufacturers may refer to an element by different names, and this document does not intend to distinguish between elements that differ in name but not function. In the following description and claims, the terms "comprise", "include" and "have" are open-ended fashion, so they should be interpreted as "including but not limited to . . . ".

The ordinal numbers used in the specification and the appended claims, such as "first", "second", etc., are used to describe the elements of the claims. It does not mean that the element has any previous ordinal numbers, nor does it represent the order of a certain element and another element, or the sequence in a manufacturing method. These ordinal numbers are just used to make a claimed element with a certain name be clearly distinguishable from another claimed element with the same name.

Spatially relative terms, such as "above", "on", "beneath", "below", "under", "left", "right", "before", "front", "after", "behind" and the like, used in the following embodiments just refer to the directions in the drawings and are not intended to limit the present disclosure.

In addition, when one element or layer is "on" or "above" another element or layer or is "connected to" the another element or layer, it may be understood that the element or layer is directly on the another element or layer or directly connected to the another element or layer, and alternatively, another element or layer may be between the element or layer and the another element or layer (indirectly). On the contrary, when the element or layer is "directly on" the another element or layer or is "directly connected to" the another element or layer, it may be understood that there is no intervening element or layer between the element or layer and the another element or layer. Also, the term "electrically connected" or "coupled" includes means of direct or indirect electrical connection.

As disclosed herein, the terms "approximately", "essentially", "about", or "substantially" generally mean within 20%, 10%, 5%, 3%, 2%, 1%, or 0.5% of the reported numerical value or range. The quantity disclosed herein is an approximate quantity, that is, without a specific description of "approximately", "essentially", "about", or "substantially", the quantity may still include the meaning of "approximately", "essentially", "about", or "substantially".

It should be understood that according to the following embodiments, features of different embodiments may be replaced, recombined or mixed to constitute other embodiments without departing from the spirit of the present disclosure. The features of various embodiments may be mixed arbitrarily and used in different embodiments without departing from the spirit of the present disclosure or conflicting.

In the present disclosure, the length, thickness, width, height, and distance may be measured by using an optical microscope (OM), a scanning electron microscope (SEM) or other approaches, but not limited thereto.

Unless otherwise defined, all terms (including technical and scientific terms) used herein have the same meaning as commonly understood by those skilled in the art. It should be understood that these terms, such as those defined in commonly used dictionaries, should be interpreted as having meaning consistent with the relevant technology and the background or context of the present disclosure, and should not be interpreted in an idealized or excessively formal way, unless there is a special definition in the embodiments of the present disclosure.

A bio sensing device (or an electronic device) of the present disclosure may be a bendable, stretchable and/or flexible electronic device, but not limited thereto. In the present disclosure, the bio sensing device may include a sensing device, alight emitting device, a display device, an antenna device, a touch device, a tiled device or other suitable devices, but not limited thereto. The sensing device may be mainly a sensing device of optical type, but not limited thereto. The sensing device may for example be used for detecting changes in capacitances, light, heat or ultrasound, but not limited thereto. The sensing device may, for example, include a biosensor, a touch sensor, a fingerprint sensor, other suitable sensors or any combination of sensors mentioned above. The display device may, for example, be applied to a laptop, a public display, a tiled display, a vehicle display, a touch display, a television, a monitor, a smartphone, a tablet, a light source module, a lighting device or an electronic device applied to the above product, but not limited thereto. The display device may, for example, include a light emitting element, a fluorescent material, a phosphor material, other suitable display mediums, or any combination thereof, but not limited thereto. The light emitting element may, for example, include an organic light emitting diode (OLED), a mini light emitting diode (mini-LED) or a micro light emitting diode (micro LED), a quantum dot light emitting diode (e.g., QLED or QDLED), other suitable elements or any combination of elements mentioned above. The antenna device may, for example, include liquid crystal antenna or antennas of other types, but not limited thereto. The tiled device may, for example, include a tiled display device or a tiled antenna device, but not limited thereto. Furthermore, the appearance of the bio sensing device may be rectangular, circular, polygonal, a shape with curved edges, curved or other suitable shapes, but not limited thereto. The electronic device may have peripheral systems such as a driving system, a control system, a light source system, a shelf system, etc. The bio sensing device may include electronic elements, in which the electronic elements may include a passive element and an active element, and for example include a capacitor, a resistor, an inductor, a diode, a transistor, a sensor, etc. It is noted that the bio sensing device of the present disclosure may be any combination of the above-mentioned devices, but not limited thereto.

Figure 2:
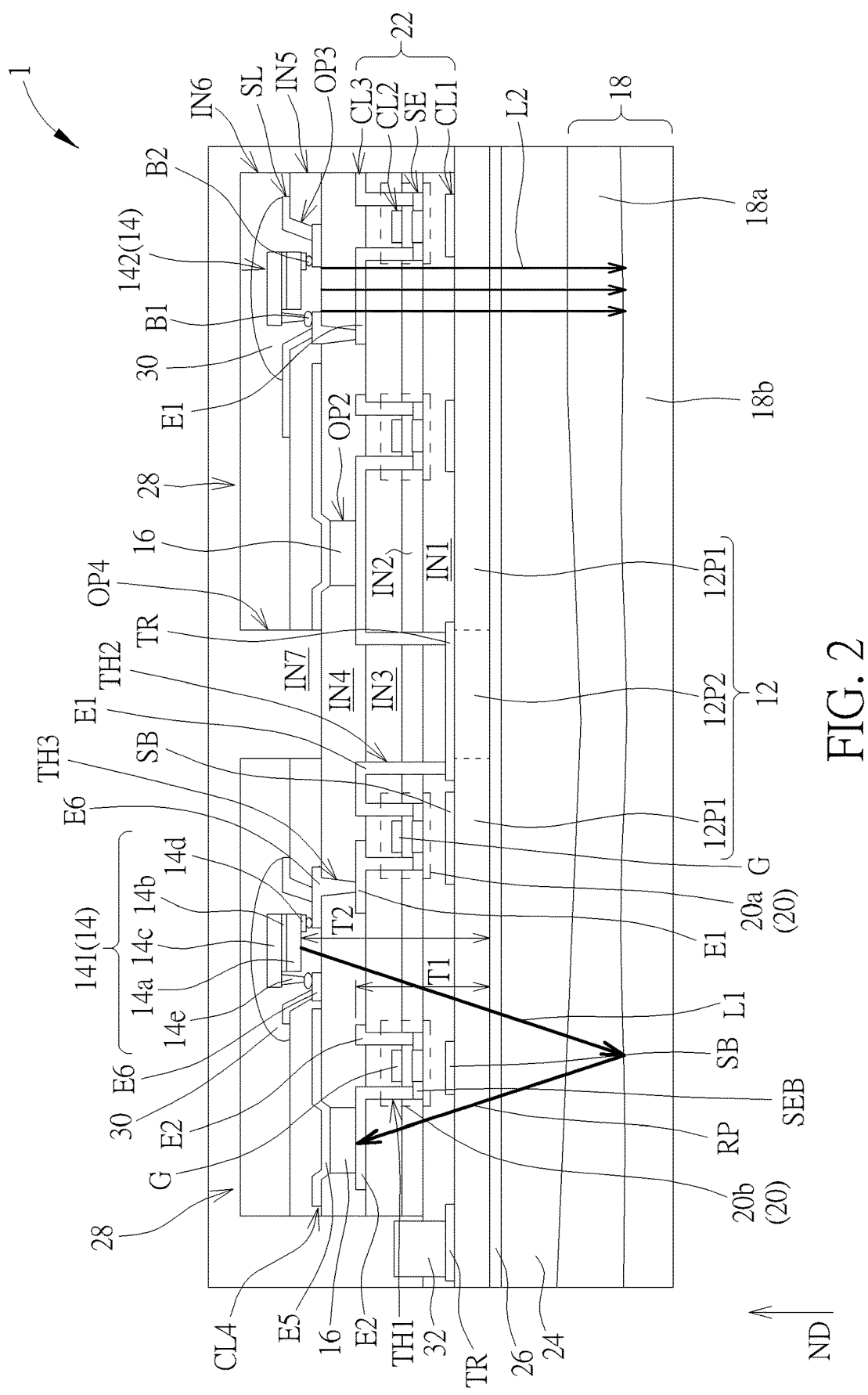
FIG. 2 schematically illustrates a sectional view of the bio sensing device according to an embodiment of the present disclosure.
Figure 3:
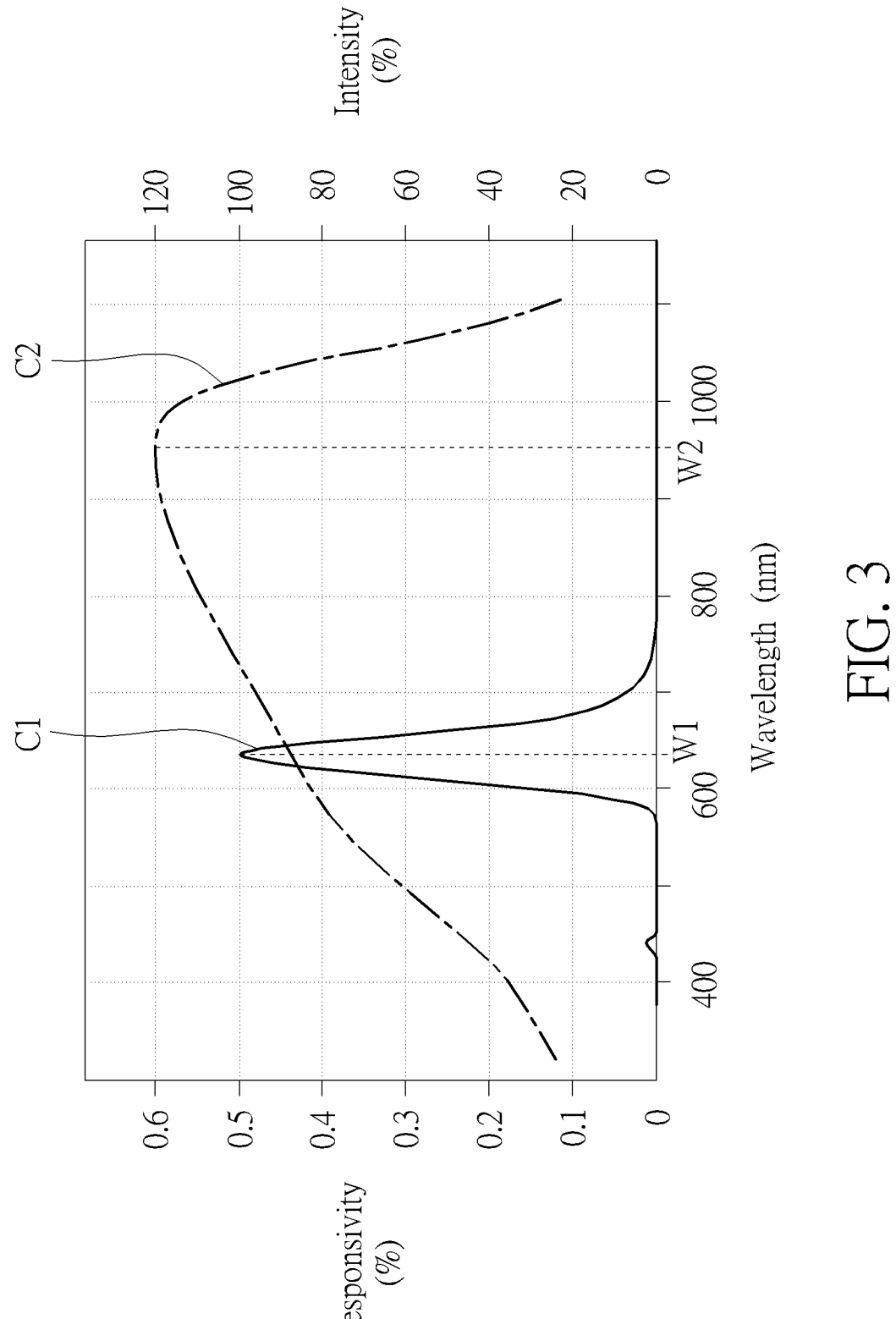
FIG. 3 is a schematic diagram of a spectrum of a light emitting element and a spectral responsivity of an optical sensor according to an embodiment of the present disclosure.

Refer to FIG. 1 to FIG. 3. FIG. 1 schematically illustrates a top view of a bio sensing device placed on a skin layer of a user according to a first embodiment of the present disclosure. FIG. 2 schematically illustrates a sectional view of the bio sensing device according to an embodiment of the present disclosure. FIG. 3 is a schematic diagram of a spectrum of a light emitting element and a spectral responsivity of an optical sensor according to an embodiment of the present disclosure. As shown in FIG. 1 and FIG. 2, the bio sensing device 1 may include a medium layer 12, a light emitting element 14 and an optical sensor 16. The light emitting element 14 is configured to emit a light L1 toward a user's skin layer 18, wherein the light L1 has a maximum intensity in a first wavelength, and the light L1 may pass through the medium layer 12. The optical sensor 16 may be configured to receive a reflected part RP of the light L1 from the user's skin layer 18, wherein the reflected part RP of the light L1 passes through the medium layer 12, and the medium layer 12 has a first transmittance greater than 60% with respect to the first wavelength. It should be noted that, since the medium layer 12 has the first transmittance greater than 60% (the first transmittance>60%) at the first wavelength at which the light L1 has the maximum intensity, the influence of the medium layer 12 on the detection of biological information may be reduced or avoided. The first transmittance of the medium layer 12 with respect to the first wavelength may be, for example, greater than 80% (the first transmittance>80%), but not limited thereto.

Specifically, as shown in FIG. 2, the medium layer 12 is a layer located between the light emitting element 14 and the skin layer 18 of the user and between the optical sensor 16 and the skin layer 18. In the embodiment of FIG. 2, the medium layer 12 may be, for example, a substrate for disposing the light emitting element 14 and the optical sensor 16. For example, the material of the medium layer 12 may include a flexible substrate or a rigid substrate. The flexible substrate may, for example, include polyethylene terephthalate (PET), polyimide (PI), polycarbonate (PC), poly(methyl methacrylate) (PMMA) or other suitable substrates. The rigid substrate may, for example, include a thinned glass or other suitable substrates. The present disclosure is not limited thereto, and the material of the medium layer 12 may be adjusted according to a range of the first wavelength of the light L1. For example, when the first wavelength ranges from 600 nanometers (nm) to 750 nm, the medium layer 12 may include yellow PI or other suitable materials. In some embodiments, the medium layer 12 may be, for example, a single-layer or multi-layer structure.

In the embodiment of FIG. 1 and FIG. 2, the medium layer 12 may be, for example, a patterned substrate, such that the medium layer 12 is a stretchable medium layer, but not limited thereto. For example, the medium layer 12 may include a plurality of island portions 12P1 and at least one bridge portion 12P2, wherein the island portions 12P1 are separated from each other, and the bridge portion 12P2 may connect at least two of the island portions 12P1 to each other. When the medium layer 12 is stretched (e.g., being stretched along a direction D1 or a direction D2), the bridge portion 12P2 may move to pull the island portions 12P1, such that the island portions 12P1 may move or rotate to stretch or bend the bio sensing device 1 while reducing the possibility of damage to the bio sensing device 1. For example, in FIG. 1, at least three corners of one of the island portions 12P1 may be respectively connected to the corresponding bridge portions 12P2, and the bridge portions 12P2 connected to the one of the island portions 12P1 may be respectively connected to other different island portions 12P1, but not limited thereto. In other words, the island portions 12P1 and the bridge portions 12P2 may surround and form a plurality of openings OP1, and the sizes of the openings OP1 may change as the bio sensing device 1 is stretched. In some embodiments, the structure shown in FIG. 1 may be regarded as a unit structure, and a top view pattern of the medium layer 12 may include, for example, a plurality of unit structures connected to each other, but not limited thereto. The top view pattern of the medium layer 12 of the present disclosure is not limited thereto and may be adjusted according to the requirements.

As shown in FIG. 1 and FIG. 2, the light emitting element 14 and the optical sensor 16 may be disposed on the medium layer 12, for example, formed on the medium layer 12 by processes. In an embodiment, one of the light emitting elements 14 may not be overlapped with the corresponding optical sensor 16 in a normal direction ND of the medium layer 12. The number of the light emitting elements 14 and the number of the optical sensors 16 in the bio sensing device 1 may be at least one, but not limited thereto. In an embodiment, one of the light emitting elements 14 and a corresponding one of the optical sensors 16 may be disposed on at least one of the island portions 12P1. In the embodiment of FIG. 1, one of the light emitting elements 14 and the corresponding one of the optical sensors 16 may be disposed on the same island portion 12P1, but not limited thereto. In some embodiments, one of the light emitting elements 14 and the corresponding one of the optical sensors 16 may be disposed on different island portions 12P1, but not limited thereto. In some embodiments, the number of the light emitting elements 14 and the number of the optical sensors 16 disposed on the same island portion 12P1 may be different. In some embodiments, one of the light emitting elements 14 may not correspond to one of the optical sensors 16 and may correspond to a plurality of the optical sensors 16. Alternatively, a plurality of the light emitting elements 14 may correspond to one of the optical sensors 16, but not limited thereto. As disclosed herein, the normal direction ND of the medium layer 12 may be, for example, a normal direction of a surface of the medium layer 12 opposite to the skin layer 18 when the bio sensing device 1 is not bent.

Figure 6:
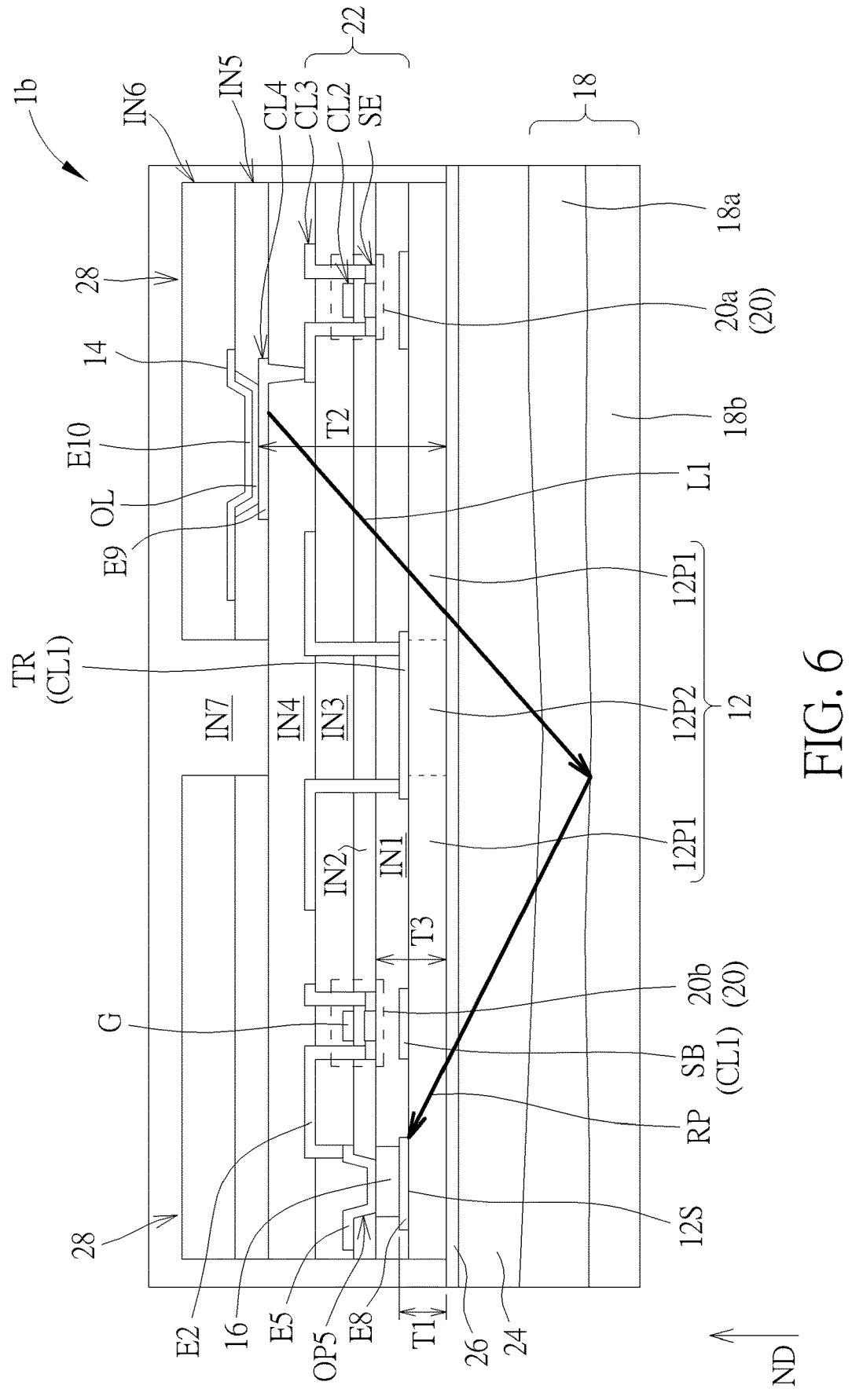
FIG. 6 schematically illustrates a sectional view of a bio sensing device according to a second variant embodiment of the first embodiment of the present disclosure.

In the embodiment of FIG. 2, the light emitting element 14 may, for example, emit light L1 towards the medium layer 12 (or the circuit layer 22), and the light L1 is mainly used to detect biological information, but not limited thereto. In some embodiments, besides the light L1, the light emitting element 14 may further emit light toward a side of the light emitting element 14 opposite to the medium layer 12, but not limited thereto. The light emitting element 14 in the embodiment of FIG. 2 is an inorganic light emitting diode as an example, but not limited thereto. For example, the light emitting element 14 may include a semiconductor layer 14a, an active layer 14b and a semiconductor layer 14c stacked in sequence, wherein the active layer 14b is disposed between the semiconductor layer 14a and the semiconductor layer 14c and used for generating the light L1. In addition, the light emitting element 14 may further include a bonding pad 14d and a bonding pad 14e respectively disposed on surfaces of the semiconductor layer 14a and the semiconductor layer 14c. In this embodiment, the light emitting element 14 is disposed on the medium layer 12 by a flip-chop method in a way of the bonding pad 14d and the bonding pad 14e facing the medium layer 12, but not limited thereto. In some embodiments, in order to emit the light L1 toward the medium layer 12, a reflective layer may be optionally formed on the semiconductor layer 14c. In some embodiments, the light emitting element 14 in FIG. 2 may be replaced by an organic light emitting diode, as shown in FIG. 6.

The first wavelength of the light L1 generated by the light emitting element 14 may be determined according to the biological information to be detected. For example, when the bio sensing device 1 is used to detect blood oxygen concentration (or blood oxygen saturation level) in blood, the first wavelength may, for example, range from 600 nm to 750 nm (600 nm≤the first wavelength≤750 nm) or from 850 nm to 1000 nm (850 nm≤the first wavelength≤1000 nm). In some embodiments, the first wavelengths of the light L1 from different light emitting elements 14 may respectively range from 600 nm to 750 nm and from 850 nm to 1000 nm, but not limited thereto.

As shown in FIG. 2, since the optical sensor 16 is used to receive the light L1 of the first wavelength, the optical sensor 16 may absorb the reflected part RP of the light L1 from the skin layer 18 of the user and convert it into an electrical signal. The optical sensor 16 may have a maximum responsivity in a second wavelength, and the medium layer 12 may have a second transmittance higher than a certain percentage with respect to the second wavelength. The second transmittance may for example be greater than 60% (the second transmittance>60%), or even greater than 800 (the second transmittance>80%) with respect to the second wavelength. For example, when the bio sensing device 1 is used to detect blood oxygen concentration, the second wavelength may range from 600 nm to 750 nm (600 nm≤the second wavelength≤750 nm) or range from 850 nm to 1000 nm (850 nm≤the second wavelength≤1000 nm). A sensing material used in the optical sensor 16 may determine its responsivities at different wavelengths. In the application of detecting the blood oxygen concentration, the optical sensor 16 may, for example, include a silicon-based sensor. The responsivity may be defined, for example, as a current value (A/W) measured from the optical sensor 16 irradiated by a certain intensity of light. It should be noted that a suitable material for the medium layer 12 may be determined to improve detection accuracy by measuring the first wavelength of the light emitting element 14 and/or the second wavelength of the optical sensor 16.

For example, as shown in FIG. 3, a curve C1 and a curve C2 respectively represent a spectral curve of the light emitting element 14 and a spectral responsivity curve of the optical sensor 16. The coordinate axis on the right of FIG. 3 represents the intensity of the spectral curve of the light emitting element 14, and the coordinate axis on the left of FIG. 3 represents the responsivity of the spectral responsivity curve of the optical sensor 16. In FIG. 3, the curve C1 may have the maximum intensity at the first wavelength W1, and the first wavelength W1 may be, for example, 636 nm in the wavelength band from 600 nm to 750 nm, but not limited thereto. The curve C2 may have a maximum responsivity at the second wavelength W2, and the second wavelength W2 may, for example, be 975 nm in the wavelength band from 850 nm to 1000 nm, but not limited thereto. In other words, the first wavelength W1 and the second wavelength W2 may be located in two different wavelength bands as mentioned above, but not limited thereto. The first wavelength W1 of the light emitting element 14 and the second wavelength W2 of the optical sensor 16 are not limited to the mentioned above and may be adjusted according to the requirements or element characteristics. In some embodiments, in order to receive high responsivity of light L1 by the optical sensor 16, the second wavelength W2 and the first wavelength W1 may be located in the same wavelength band as mentioned above or may be the same or close to each other, but not limited thereto.

In some embodiments, the optical sensor 16 may include a photodiode, an organic photodiode (OPD) or other suitable optical sensing elements. The optical sensor 16 of FIG. 2 is exemplary and not limited thereto. For example, when the optical sensor 16 includes the photodiode, the optical sensor 16 may include a stacked structure of two semiconductor layers with different conductivity types, but not limited thereto. When the optical sensor 16 includes the organic photodiode, the optical sensor 16 may include an organic semiconductor layer for detecting light. In some embodiments, the optical sensor 16 may further include an upper electrode and a lower electrode, and the organic semiconductor layer is interposed between the upper electrode and the lower electrode, or the optical sensor 16 may not include the upper electrode and the lower electrode, but not limited thereto. In some embodiments, the positions of the electrodes of the optical sensor 16 may be adjusted as required. In some embodiments, the upper electrode of the optical sensor 16 opposite to a light incident surface receiving the light may be, for example, a reflective electrode, but not limited thereto.

In the embodiment of FIG. 2, a distance T1 between the optical sensor 16 and the medium layer 12 may be less than a distance T2 between the light emitting element 14 and the medium layer 12, but not limited thereto. The distance T1 between the optical sensor 16 and the medium layer 12 may for example be defined as a distance between a bottom surface of the semiconductor layer (or the organic semiconductor layer) of the optical sensor 16 closest to the medium layer 12 and a bottom surface of the medium layer 12 facing the skin layer 18. When the light emitting element 14 is the inorganic light emitting diode, the distance T2 between the light emitting element 14 and the medium layer 12 may for example be defined as a distance between a bottom surface of the semiconductor layer 14a of the light emitting element 14 closest to the medium layer 12 and the bottom surface of the medium layer 12 facing the skin layer 18, but not limited thereto.

The skin layer 18 of the user may be, for example, a biological skin or other similar biological features. As shown in FIG. 2, the skin layer 18 of the user may be, for example, human skin, which includes an epidermis 18a and a blood vessel layer 18b. The blood vessel layer 18b may include dermis and hypodermis. When the light L1 enters blood vessels in the dermis or the hypodermis, a part of the light L1 of some wavelengths is absorbed by the blood in the blood vessels. For example, since absorbances of oxyhemoglobin ($HbO_2$) and deoxyhemoglobin (Hb) in the blood with respect to the light L1 of the first wavelength are obviously different, the blood oxygen concentration may be calculated by measuring the intensity variance of the reflected part RP of the light L1 with the first wavelength after entering the blood vessel and being reflected by the blood vessel. Alternatively, when heart contracts and relaxes, the absorbance of arterial blood with respect to the light L1 may changes periodically, so the heartbeat may be detected by measuring the intensity variance of the reflected part RP of the light L1.

Figure 4:
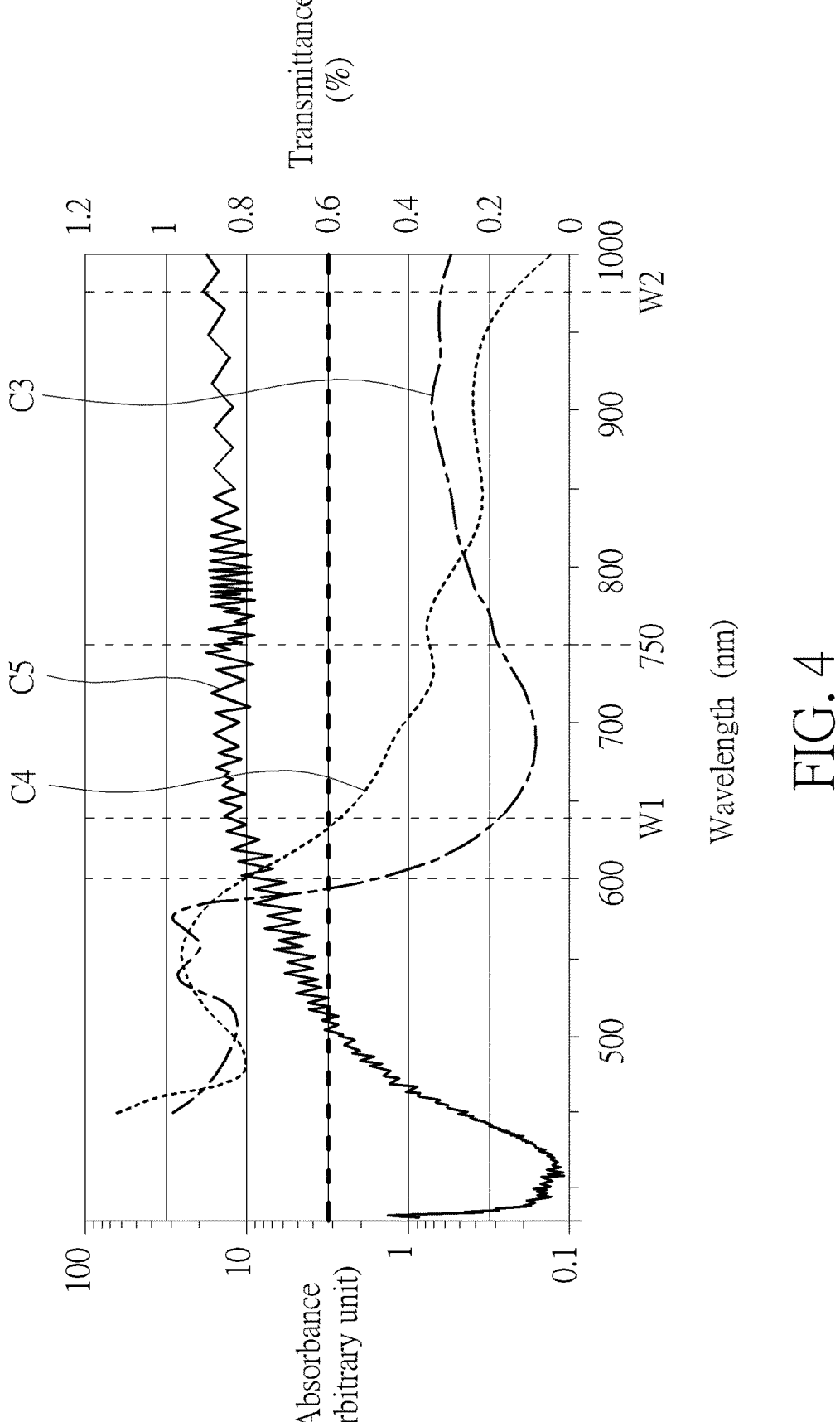
FIG. 4 is a schematic diagram of absorption spectra of oxyhemoglobin and deoxyhemoglobin in blood and a transmission spectrum of the medium layer according to an embodiment of the present disclosure.

Refer to FIG. 4, which is a schematic diagram of absorption spectra of oxyhemoglobin and deoxyhemoglobin in blood and a transmission spectrum of the medium layer according to an embodiment of the present disclosure. As shown in FIG. 4, a curve C3 and a curve C4 respectively represent the absorption spectra of oxyhemoglobin and deoxyhemoglobin in the blood, and the coordinate axis on the left of FIG. 4 represents the absorbance. According to the curve C3 and the curve C4 in FIG. 4, there is a greater difference between the absorbances of oxyhemoglobin and deoxyhemoglobin with respect to the light in the wavelength bands from 600 nm to 750 nm and from 850 nm to 1000 nm. Therefore, designing the first wavelength of the light L1 generated by the light emitting element 14 in any one of the above two wavelength bands may help to detect the difference between amounts of oxyhemoglobin and deoxyhemoglobin, thereby calculating blood oxygen concentration in the blood.

In addition, a curve C5 is the transmission spectrum of the medium layer 12, and the coordinate axis on the right of FIG. 4 represents the transmittance. According to the curve C5 in FIG. 4, the medium layer 12 may have a transmittance greater than 60% in the wavelength band from 600 nm to 750 nm and/or in the wavelength band from 850 nm to 1000 nm. For example, when the first wavelength W1 shown in FIG. 3 is in the wavelength band from 600 nm to 750 nm, the first transmittance of the medium layer 12 at the first wavelength W1 may be, for example, greater than 60%, or even greater than 80%, such that the influence of the medium layer 12 on the light L1 emitted toward the skin layer 18 may be reduced or avoided. Furthermore, when the second wavelength W2 shown in FIG. 3 is located in the wavelength band from 850 nm to 1000 nm, the second transmittance of the medium layer 12 at the second wavelength W2 may be, for example, greater than 60%, or even greater than 80% (the second transmittance>80%), so as to reduce or prevent the medium layer 12 from affecting optical signal amount detected by the optical sensor 16. The matching of the transmission spectrum of the medium layer 12 with the first wavelength W1 and/or the second wavelength W2 may increase the intensity of the light L1 and its reflected part RP passing through the medium layer 12, thereby improving the detection accuracy of the biological information.

The bio sensing device 1 of the present disclosure may not be limited to detecting the blood oxygen concentration. In some embodiments, the bio sensing device 1 may, for example, be used to detect electroencephalogram (EEG), electrooculogram (EOG), electromyogram (EMG), electrocardiogram (ECG), airflow or respiration efforts, neurofeedback and biofeedback, or other physiological signals or detect other suitable biological information of the user.

As shown in FIG. 1, the bio sensing device 1 may further include a plurality of transistor circuits 20, and at least one of the transistor circuits 20 may be disposed on the same island portion 12P1 as the corresponding light emitting element 14 and the corresponding optical sensor 16 and be used to control the corresponding light emitting element 14 and the corresponding optical sensor 16. As an example of corresponding to the same island portion 12P1, the transistor circuit 20, the light emitting element 14 and the optical sensor 16 may not be at least partially overlapped with one another in the normal direction ND, so as to reduce the influence on the intensity of the light L1 used for detecting the biological information. In the embodiment of FIG. 1, the transistor circuit 20 may not be overlapped with the light emitting element 14 and the optical sensor 16 in the normal direction ND, but not limited thereto. In some embodiments, the transistor circuit 20 may be partially overlapped with the light emitting element 14 and/or the optical sensor 16 in the normal direction ND, but not limited thereto. It should be noted that, in order to clearly show the relationship among the positions of the light emitting element 14, the optical sensor 16 and the transistor circuit 20 in the normal direction ND, the light emitting element 14, the optical sensor 16 and the transistor circuit 20 shown in FIG. 1 respectively take rectangular patterns as an example, but not limited thereto. The relationship among the positions of the light emitting element 14, the optical sensor 16 and the transistor circuit 20 in the normal direction ND is not limited to that shown in FIG. 1. In some embodiments, a portion of the transistor circuit 20 may be located, for example, between the light emitting element 14 and the optical sensor 16. Alternatively, the positions of the light emitting element 14, the optical sensor 16 and the transistor circuit 20 may be adjusted according to requirements.

In the embodiment of FIG. 2, the transistor circuits 20 may include a first transistor 20a directly connected to the corresponding light emitting element 14. The first transistor 20a may be disposed on the same island portion 12P1 as the corresponding light emitting element 14, but not limited thereto. In some embodiments, the first transistor 20a and the corresponding light emitting element 14 may be disposed on different island portions 12P1. In some embodiments, a gate electrode G of the first transistor 20a may not be overlapped with the corresponding light emitting element 14 in the normal direction ND, so as to reduce the influence of the first transistor 20a on the light L1. Alternatively, the entire first transistor 20a may not be overlapped with the corresponding light emitting element 14 in the normal direction ND, but not limited thereto. Herein, when an element is referred to as being "directly connected" to another element, it should be understood that under a circuit architecture, the element and the another element are coupled to each other at the same node in the circuit, and the element may be electrically connected to the another element through a conductive layer. The definition of the term "directly connected" may be applied to the following contents and will not be repeated herein.

As shown in FIG. 2, in some embodiments, the transistor circuits 20 may further include a second transistor 20b directly connected to the corresponding optical sensor 16c. The second transistor 20b may be disposed on the same island portion 12P1 as the corresponding optical sensor 16, but not limited thereto. In some embodiments, the second transistor 20b and the corresponding optical sensor 16 may be disposed on different island portions 12P1. In some embodiments, the gate electrode G of the second transistor 20b may not be overlapped with the corresponding optical sensor 16 in the normal direction ND, so as to reduce the blocking of the second transistor 20b to the reflected part RP. Alternatively, the entire second transistor 20b may not be overlapped with the corresponding optical sensor 16 in the normal direction ND, but not limited thereto.

The specific structure of the bio sensing device 1 of this embodiment will be further described as follows, but not limited thereto. As shown in FIG. 2, the bio sensing device 1 may further include a circuit layer 22 disposed on the medium layer 12, and the circuit layer 22 may include the transistor circuits 20. In the embodiment of FIG. 2, the circuit layer 22 may include, for example, a conductive layer CL1, an insulating layer IN1, a semiconductor layer SE, an insulating layer IN2, a conductive layer CL2, an insulating layer IN3, and a conductive layer CL3, but not limited thereto.

As shown in FIG. 2, the conductive layer CL1 may be disposed on the medium layer 12. The conductive layer CL1 may include a plurality of traces TR and a plurality of light shielding blocks SB. The traces TR may, for example, be disposed on the corresponding bridge portion 12P1 of the medium layer 12 to couple elements on different island portions 12P1 or couple the elements on the island portions 12P1 to the outside. The light shielding block SB may be used to reduce the influence of the light L1 or the reflected part RP on the operation of the transistors. One of the light shielding blocks SB may be disposed corresponding to one of the transistors. The conductive layer CL1 may, for example, include an opaque conductive material, but not limited thereto. In some embodiments, the light shielding block SB may be formed of a non-conductive opaque material, but not limited thereto.

The insulating layer IN1 may be disposed on the conductive layer CL1. The insulating layer IN1 may, for example, be used as a buffer layer of the bio sensing device 1 to block moisture and/or oxygen from the outside, thereby reducing the possibility of damage to elements in the bio sensing device 1 due to moisture and/or oxygen.

The semiconductor layer SE may be disposed on the insulating layer IN1, and the semiconductor layer SE may include a plurality of semiconductor blocks SEB respectively disposed on the light shielding blocks SB. Two ends of one of the semiconductor blocks SEB may be doped with dopant and respectively serve as a drain region and a source region of one of the transistors (e.g., the first transistor 20a and/or the second transistor 20b), and a portion of the semiconductor block SEB located between the two ends may serve as a channel region of the transistor. One of the semiconductor blocks SEB may, for example, be overlapped with one of the light shielding blocks SB in the normal direction ND, so that the light shielding block SB may reduce light entering the semiconductor block SEB, but not limited thereto. The insulating layer IN2 may be disposed on the semiconductor layer SE and may be used as a gate insulating layer of one of the transistors. The conductive layer CL2 may be disposed on the insulating layer IN2 and includes a plurality of gate electrodes G. One of the gate electrodes G, a part of the insulating layer IN2 and one of the semiconductor blocks SEB may form one of the transistors, but not limited thereto. The material of the semiconductor layer SE includes, for example, silicon or metal oxide, such as low temperature polysilicon (LTPS) semiconductor or amorphous silicon (a-Si) semiconductor, indium gallium zinc oxide (IGZO) semiconductor or other suitable semiconductors, but not limited thereto. In some embodiments, the semiconductor blocks SEB of different transistors may include different materials, for example, the semiconductor block SEB of one of the transistors includes the low temperature polysilicon semiconductor, and the semiconductor block SEB of another of the transistors includes the metal oxide semiconductor.

The insulating layer IN3 may be disposed on the conductive layer CL2, and the insulating layer IN3 and the insulating layer IN2 may have a plurality of through holes TH1 respectively exposing the ends of the semiconductor blocks SEB. The conductive layer CL3 is disposed on the insulating layer IN2 and may include a plurality of electrodes E1 and a plurality of electrodes E2. Two of the electrodes E1 may be coupled to the drain region and the source region of the first transistor 20a through two of the through holes TH1, respectively. Two of the electrodes E2 may be coupled to the drain region and the source region of the second transistor 20b through another two of the through holes TH1, respectively. The insulating layer IN3, the insulating layer IN2 and the insulating layer IN1 may have a plurality of through holes TH2 respectively exposing ends of the traces TR, such that one of the electrodes E1 and/or one of the electrode E2 may be coupled to one of the traces TR through the through holes TH2, thereby coupling the transistors located on different island portions 12P1 to each other. In some embodiments, the conductive layer CL1, the conductive layer CL2 and/or the conductive layer CL3 may further optionally include electrodes, signal lines (such as data lines) or other conductive elements, but not limited thereto. The conductive layer CL1, the conductive layer CL2 and the conductive layer CL3 may include metals, transparent conductive materials or other suitable conductive materials according to requirements. It should be noted that the structure of the circuit layer 22 shown in FIG. 2 is exemplary, and the present disclosure is not limited thereto.

As shown in FIG. 2, the optical sensors 16 may be respectively disposed on the corresponding electrodes E2, and thus, may be coupled to the second transistors 20b through the electrodes E2. In the embodiment of FIG. 2, the bio sensing device 1 may further include an insulating layer IN4 disposed on the circuit layer 22 and having a plurality of openings OP2 exposing corresponding optical sensors 16 respectively, but not limited thereto. The insulating layer IN4 may further have a plurality of through holes TH3 respectively exposing the corresponding electrodes E1. In the embodiment of FIG. 2, the conductive layer CL3 including the electrodes E1 and the electrodes E2 may include the transparent conductive material, such that the reflected part RP reflected from the skin layer 18 may pass through the electrodes E2 and be detected by the optical sensors 16, but not limited thereto. In some embodiments, when one of the electrodes E1 coupled to one of the light emitting elements 14 is overlapped with the light emitting element 14 in the normal direction ND, the influence of the electrode E1 on the light L1 may be reduced, but not limited thereto.

In FIG. 2, the bio sensing device 1 may further include a plurality of island structures 28 disposed on the insulating layer IN4, and each island structure 28 may respectively be disposed corresponding to one of the island portions 12P1 in the normal direction ND, for example, may be overlapped with the island portion 12P1 in the normal direction ND. For example, the island structures 28 may include a conductive layer CL4, an insulating layer IN5, an insulating layer IN6, and the light emitting elements 14. The conductive layer CL4 may be disposed on the insulating layer IN4 and include a plurality of electrodes E5 and a plurality of electrodes E6. One of the electrodes E5 is disposed on the corresponding optical sensor 16 and coupled to the optical sensor 16 through one of the openings OP2. In some embodiments, when all the electrodes of the optical sensor 16 face the circuit layer 22, the conductive layer CL4 may not include the electrodes E5, but not limited thereto. One of the electrodes E6 may be coupled to the corresponding one of the electrodes E1 through the corresponding through hole TH3. In some embodiments, the conductive layer CL4 may include a reflective conductive material, such that one of the electrodes E5 located on the corresponding optical sensor 16 may be used to reflect the reflected part RP that is not absorbed by the optical sensor 16, so as to enhance the intensity of signal detected by the optical sensor 16.

The insulating layer IN5 may be disposed on the conductive layer CL4 and has a plurality of openings OP3, wherein each opening OP3 may expose two corresponding electrodes E6. One of the light emitting elements 14 may be disposed in a corresponding one of the openings OP3, and the bonding pad 14d and the bonding pad 14e of the light emitting element 14 may be respectively coupled to the two corresponding electrodes E6 exposed by the corresponding openings OP3 through a conductive ball B1 and a conductive ball B2, so that the light emitting element 14 may be coupled to one of the drain region and the source region of the first transistor 20a. In the embodiment of FIG. 2, when the conductive layer CL4 includes a reflective conductive material, an opening may be between the two electrodes E6, so that the light L1 (or light L2) generated by the light emitting element 14 may pass through the opening and be emitted toward the skin layer 18, but not limited thereto. In some embodiments, the electrodes E6 may include a transparent conductive material, and in this case, the opening between the electrodes E6 may have less size. In some embodiments, the electrodes E6 and the electrodes E5 may be formed of different conductive layers, or the electrodes E5 may include the transparent conductive material. The insulating layer IN6 may be disposed on the light emitting elements 14 and the insulating layer IN5 to protect the light emitting elements 14, the optical sensors 16 and the transistor circuits 20. In some embodiments, the bio sensing device 1 may optionally include a shielding layer SL disposed on the sidewalls of the openings OP3, but not limited thereto.

In some embodiments, one of the island structures 28 may further optionally include an encapsulation layer 30 disposed between the corresponding light emitting element 14 and the insulating layer IN6 to protect the corresponding light emitting element 14. In an embodiment, the encapsulation layer 30 may be further disposed in one of the openings OP3 of the insulating layer IN5 to enhance adhesion between the corresponding light emitting element 14 and the conductive layer CL4. It should be noted that layers of the island structures 28 shown in FIG. 2 are exemplary, and the present disclosure is not limited thereto. In some embodiments, the island structures 28 may include different layers and elements according to different types of the bio sensing device 1.

In the embodiment of FIG. 2, there may be an opening OP4 between adjacent two of the island structures 28, and the opening OP4 may penetrate through the insulating layer IN5 and the insulating layer IN6, but not limited thereto. In some embodiments, a depth of the opening OP4 may be adjusted as required. In some embodiments, other openings may be between the island structures 28 and respectively correspond to the openings OP1 of the medium layer 12 shown in FIG. 1. The openings may, for example, penetrate through the insulating layer IN6, the insulating layer IN5, the insulating layer IN4, the insulating layer IN3, the insulating layer IN2 and the insulating layer IN1 to expose the corresponding openings OP1 of the medium layer 12, but not limited thereto.

As shown in FIG. 2, the bio sensing device 1 may further include an insulating layer IN7 disposed on the island structures 28 and disposed in the openings OP4. In an embodiment, the insulating layer IN7 may be, for example, a topmost layer of the bio sensing device 1. In this case, the insulating layer IN7 may include, for example, a water-repellent encapsulation material to reduce the possibility of damage to the light emitting elements 14 and/or the optical sensors 16 due to moisture and/or oxygen. With this design, there is no need to attach an additional covering substrate to the insulating layer IN7, thereby saving costs.

It should be noted that the insulating layer IN1, the insulating layer IN2, the insulating layer IN3, and the insulating layer IN4 located under the light emitting elements 14 may have similar or same refractive indices, so as to reduce the loss of the light L1 and its reflected part RP during passing through these insulating layers. For example, the insulating layer IN1, the insulating layer IN2, the insulating layer IN3 and/or the insulating layer IN4 may have a refractive index ranging from 1.6 to 2.0 (1.6≤the refractive index≤2.0), but not limited thereto. In some embodiments, the refractive index of the medium layer 12 may be selected to be close to the refractive index of the insulating layer IN1.

In some embodiments, the insulating layer IN1, the insulating layer IN2, the insulating layer IN3, the insulating layer IN4, the insulating layer IN5, the insulating layer IN6 and the insulating layer IN7 may include single-layer or multi-layer structures and may include any suitable organic or inorganic material. The organic material may include, for example, PMMA, epoxy, siloxane material, silica gel material, other suitable materials or combinations of the above materials. The inorganic material may include silicon nitride, silicon oxide, liquid glass, glass glue, titanium oxide, aluminum oxide, other suitable materials or combinations of the above materials. In some embodiments, when the insulating layer IN1, the insulating layer IN2, the insulating layer IN3, the insulating layer IN4, the insulating layer IN5, the insulating layer IN6 and the insulating layer IN7 are multi-layer structures, they may include a stacked structure of multi-layer inorganic materials or multi-layer organic materials, or a stacked structure of inorganic materials/ organic materials stacked alternately, and the present disclosure is not limited thereto.

In some embodiments, the bio sensing device 1 may optionally include a control element 32 disposed on one of the island portions 12P1 and on one side of the corresponding island structure 28 in the normal direction ND and coupled to the traces TR of the conductive layer CL1, so that the control element 32 may control the light emitting elements 14 and the optical sensors 16, but not limited thereto.

As shown in FIG. 2, the bio sensing device 1 may further include a supporting layer 24 disposed under the medium layer 12, wherein the light emitting elements 14 are disposed on a side of the medium layer 12 opposite to the supporting layer 24. The supporting layer 24 may support the medium layer 12 to increase the strength of the bio sensing device 1. In the embodiment of FIG. 2, the supporting layer 24 may be attached to the medium layer 12 through an adhesive layer 26, but not limited thereto. It should be noted that the supporting layer 24 of this embodiment may not have openings. In order to reduce the influence of the supporting layer 24 on the light L1 and its reflected part RP, a material of the supporting layer 24 may be selected from a soft material that has a high transmittance at the first wavelength and/or the second wavelength; for example, selected from a transparent soft material, but not limited thereto. In some embodiments, the adhesive layer 26 may have a transmittance greater than 80% at the first wavelength and/or the second wavelength, but not limited thereto. Since the supporting layer 24 may be placed on the medium layer 12 after the processes of forming the circuit layer 22, the optical sensors 16 and the light emitting elements 14, the material of the supporting layer 24 may be selected from a material that has a tolerable temperature lower than the process temperature for forming the circuit layer 22, the optical sensors 16 and the light emitting elements 14. As compared with the supporting layer 24, the medium layer 12 may undergo the processes of forming the circuit layer 22, the optical sensors 16 and the light emitting elements 14, so that the medium layer 12 may need to include a material that has a tolerable temperature higher than the process temperature for forming the circuit layer 22, the optical sensors 16 and the light emitting elements 14. The material of the supporting layer 24 may include PI, PET, PC, PMMA, polyvinyl chloride (PVC), polyethylene (PE), rubber or other suitable soft materials. In some embodiments, a thickness of the supporting layer 24 in the normal direction ND of the medium layer 12 may be greater than a thickness of the medium layer 12 in the normal direction ND, but not limited thereto.

It is noted that, in the bio sensing device 1 of this embodiment, since one side of the supporting layer 24 may be directly disposed or attached to the skin layer 18 after the medium layer 12 used for forming the circuit layer 22, the optical sensors 16 and the light emitting elements 14 is attached to the supporting layer 24, the bio sensing device 1 may be easily stretched and not easily damaged. Furthermore, because the light L1 from the light emitting elements 14 is emitted toward the circuit layer 22, and the optical sensors 16 receive the reflected part RP from sides of the optical sensors 16 facing the circuit layer 22, the light L1 and the reflected part RP are not easily affected by ambient light, thereby improving detection accuracy.

In some embodiments, the light emitting elements 14 of the bio sensing device 1 may also have a phototherapy function. For example, as shown in FIG. 2, the light emitting elements 14 may include a first light emitting element 141 and a second light emitting element 142, in which the first light emitting element 141 may be used to detect the biological information, and the second light emitting element 142 may be used to generate light L2 for treating the skin layer 18 of the user. With this configuration, the bio sensing device 1 may detect the condition of the skin layer 18 through the first light emitting element 141 and the optical sensor 16; for example, the bio sensing device 1 may detect a size of a wound. Then, the bio sensing device 1 may provide specific treatment, or treat the skin layer 18 with phototherapy through the second light emitting element 142; for example, treating blemishes, wounds on the skin surface, or other conditions. In some embodiments, the bio sensing device 1 may perform patterned phototherapy. For example, the bio sensing device 1 may optionally generate the light L2 with the phototherapy function for a specific region instead of generating the light L2 on the entire surface, thereby reducing power consumption or improving applicability.

The bio sensing device of the present disclosure is not limited to the above-mentioned embodiment and may have variant embodiments or other embodiments. In order to simplify the description, same elements in following variant embodiments or other embodiments as the above-mentioned embodiment may use the same reference labels. In order to easily compare the differences between the above-mentioned embodiment and variant embodiments or other embodiments, following contents describe the differences between the embodiments, and repeated parts will not be detailed again.

Figure 5:
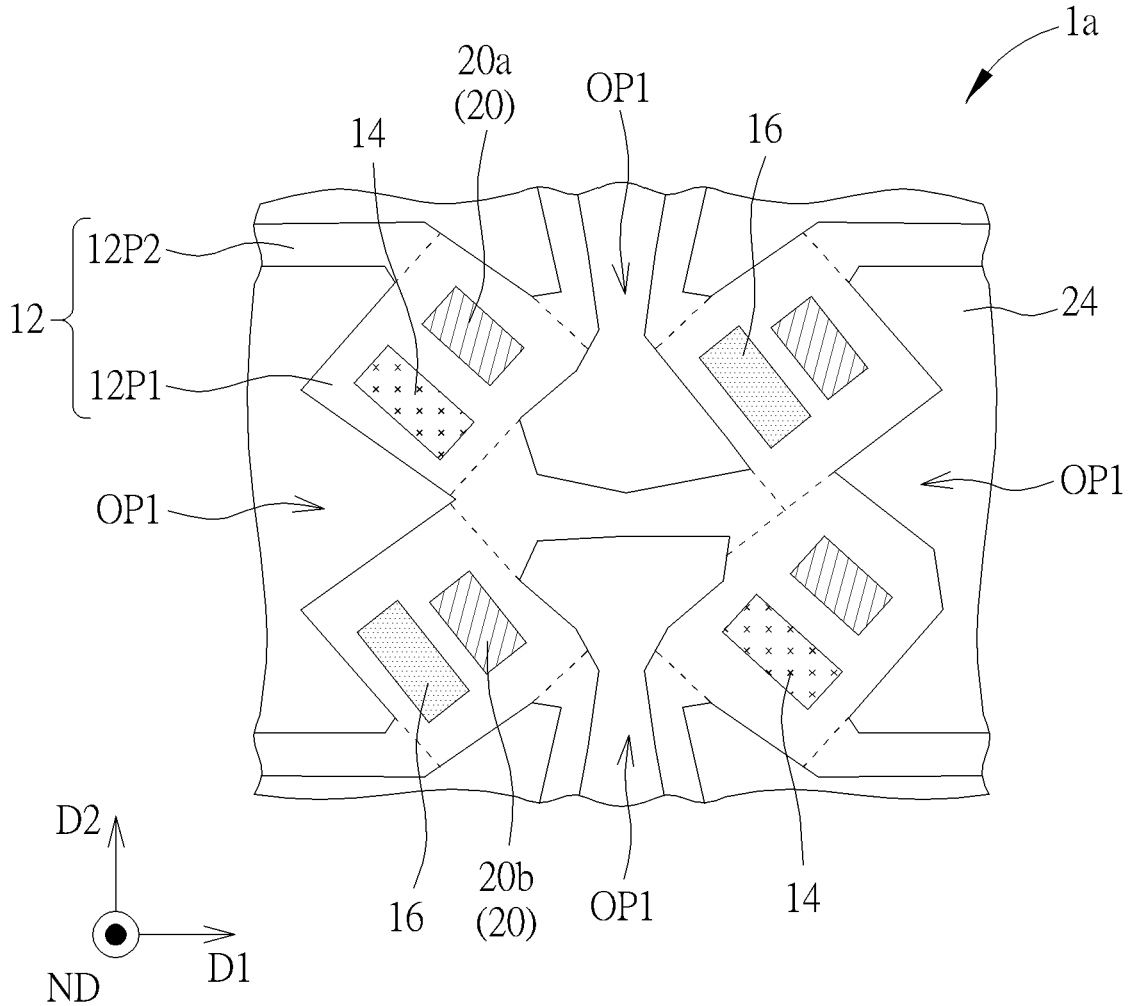
FIG. 5 schematically illustrates a top view of a bio sensing device according to a first variant embodiment of the first embodiment of the present disclosure.

Refer to FIG. 5, which schematically illustrates a top view of a bio sensing device according to a first variant embodiment of the first embodiment of the present disclosure. As shown in FIG. 5, in the bio sensing device 1*a* of this variant embodiment, the light emitting elements 14 and the optical sensors 16 may be respectively disposed on different island portions 12P1. For example, one of the light emitting elements 14 and a corresponding one of the optical sensors 16 may be respectively disposed on two adjacent island portions 12P1. The light emitting element 14 and a corresponding one of the transistor circuits 20 (e.g., the first transistor 20*a*) may be disposed on the same island portion 12P1. The optical sensor 16 and a corresponding one of the transistor circuits 20 (e.g., the second transistor 20*b*) may be disposed on the same island portion 12P1. Other parts of the bio sensing device 1*a* in this variant embodiment may use the structure of the above-mentioned embodiment or any one of following embodiments and are not mentioned repeatedly herein.

Refer to FIG. 6, which schematically illustrates a sectional view of a bio sensing device according to a second variant embodiment of the first embodiment of the present disclosure. As shown in FIG. 6, in the bio sensing device 1*b* of this variant embodiment, a distance T1 between the optical sensor 16 and the medium layer 12 may be less than a distance T3 between the gate electrode G of the second transistor 20*b* and the medium layer 12, so as to reduce the number of insulating layers through which the reflected part RP of the light L1 from the skin layer 18 to the optical sensor 16 passes, thereby improving detection accuracy.

In this variant embodiment, the bio sensing device 1*b* may further include a plurality of electrodes E8 respectively disposed under the corresponding optical sensors 16 and coupled to ends of the corresponding optical sensors 16. In FIG. 6, one of the electrodes E8 may directly contact an upper surface 12S of one of the island portions 12P1, one of the optical sensors 16 may be disposed on a corresponding one of the electrodes E8, and the insulating layer IN2 may be disposed on the optical sensor 16, but not limited thereto. In this case, the reflected part RP does not need to pass through the insulating layer IN1, the insulating layer IN2, and the insulating layer IN3, thereby reducing the loss of the reflected part RP. It should be noted that the electrodes E8 may include a transparent conductive material, such that the reflected part RP may pass through the electrodes E8. In such case, the electrodes E8 may be formed of another conductive layer instead of being formed of the conductive layer CL1 forming the light shielding blocks SB and the traces, but not limited thereto. In some embodiments, the insulating layer IN1 and the insulating layer IN2 may have an opening OP5, and the conductive layer CL2 may include an electrode E5 coupled to another end of one of the optical sensors 16 through the opening OP5, but not limited thereto. In this case, the electrode E2 coupled to the second transistor 20*b* may be coupled to the electrode E5 through a through hole of the insulating layer IN3, so as to be coupled to the optical sensor 16. The structure for coupling the second transistor 20*b* to the optical sensor 16 of the present disclosure is not limited to that shown in FIG. 6 and may be adjusted according to requirements. In some embodiments, the electrode E5 coupled to the optical sensor 16 may be formed of another conductive layer different from the conductive layer CL2.

In the variant embodiment of FIG. 6, the light emitting element 14 may be an organic light emitting diode as an example, but not limited thereto. In this case, the light emitting element 14 may include a lower electrode E9, an organic light emitting layer OL and an upper electrode E10, and the organic light emitting layer is interposed between the lower electrode E9 and the upper electrode E10. In order to emit the light L1 of the light emitting element 14 toward the skin layer 18 under the light emitting element 14, the lower electrode E9 may include a transparent conductive material, such as indium tin oxide (ITO) or other suitable materials. The upper electrode E10 may include a reflective conductive material, such as aluminum or other suitable materials, but not limited thereto. In some embodiments, when the light emitting element 14 is able to emit another light from a side of the light emitting element 14 opposite to the skin layer 18 for indicating to the user (e.g., notifying the user that the detection is in progress), the upper electrode E10 may also include the transparent conductive material. The organic light emitting diode of FIG. 6 may be applied to the light emitting element 14 hereinafter. When the light emitting element 14 is the organic light emitting diode, the distance T2 between the light emitting element 14 and the medium layer 12 may, for example, be defined as a distance between a bottom surface of the organic light emitting layer OL adjacent to the medium layer 12 and the bottom surface of the medium layer 12 facing the skin layer 18, but not limited thereto.

In the variant embodiment of FIG. 6, the positions of the light emitting elements 14 and the optical sensors 16 may use the arrangement of FIG. 5, and the light emitting elements 14 and the optical sensors 16 may be respectively disposed on different island portions 12P1, but not limited thereto. In some embodiments, the positions of the light emitting elements 14 and the optical sensors 16 in FIG. 6 may use the arrangement of other embodiments, and one of the light emitting elements 14 and one of the optical sensors 16 may be disposed on the same island portion 12P1, but not limited thereto. Other parts of the bio sensing device 1*b* of this variant may refer to the structures of the above-mentioned or following embodiments and are not detailed herein.

Figure 7:
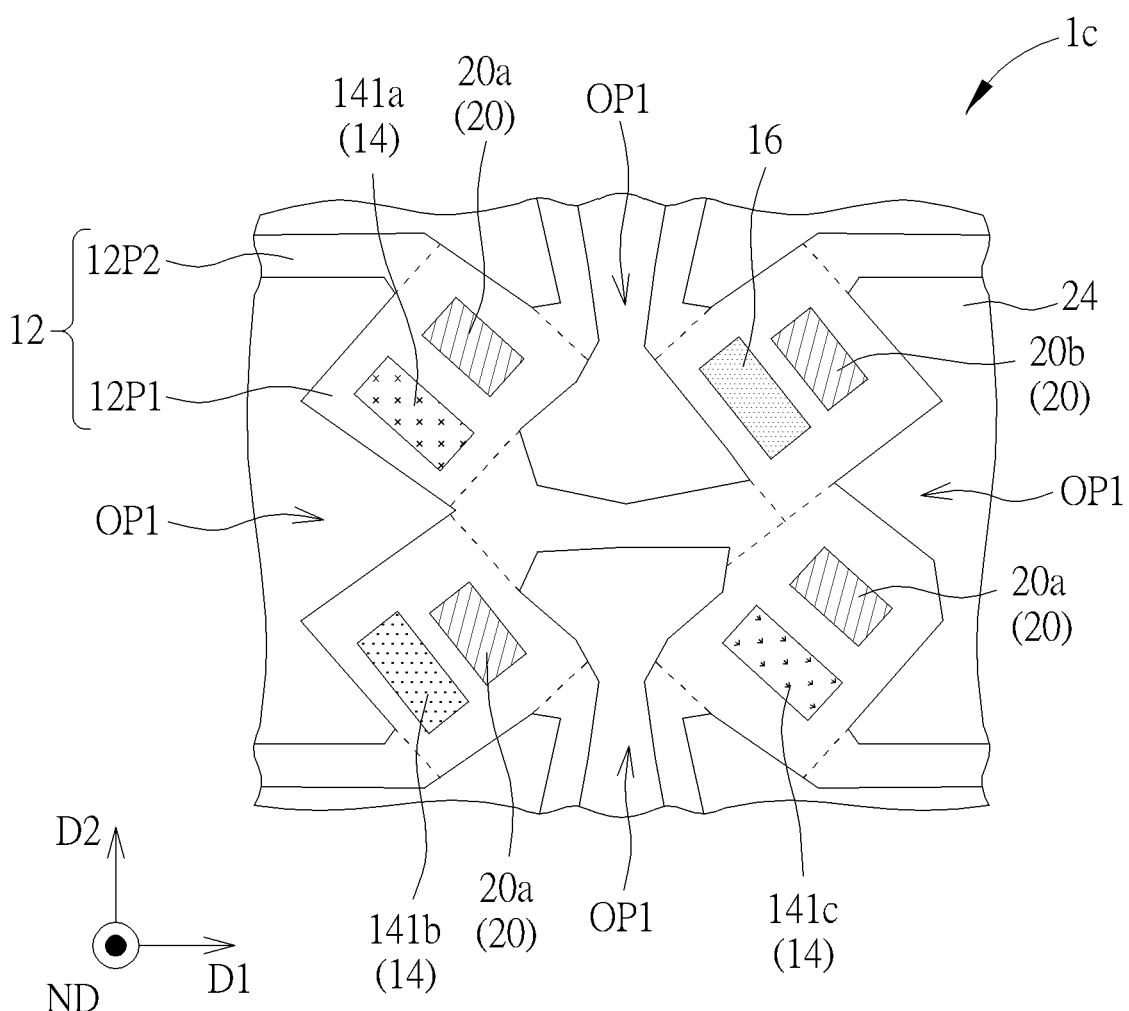
FIG. 7 schematically illustrates a top view of a bio sensing device according to a third variant embodiment of the first embodiment of the present disclosure.
Figure 8:
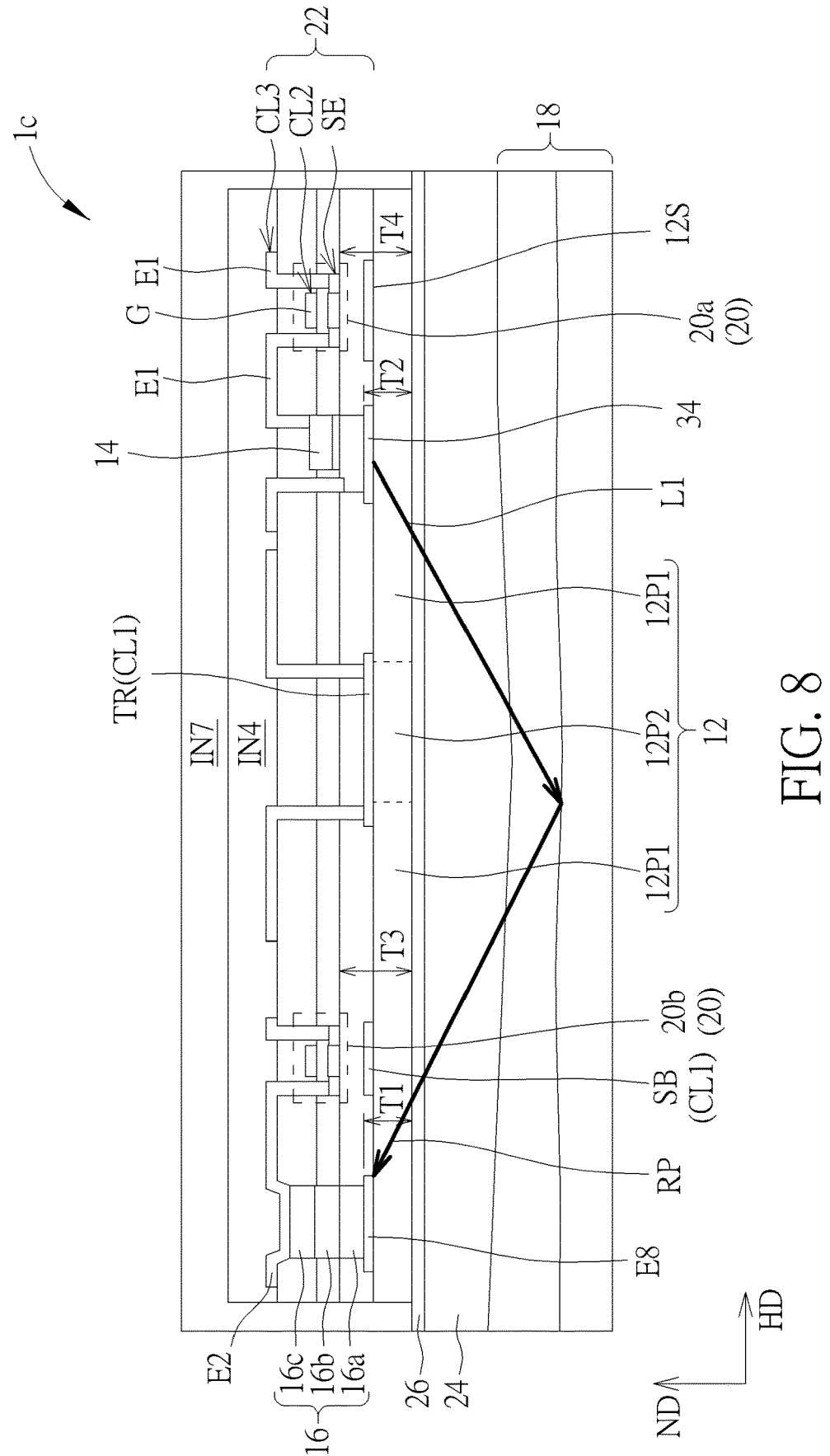
FIG. 8 schematically illustrates a sectional view of the bio sensing device according to a third variant embodiment of the first embodiment of the present disclosure.

Refer to FIG. 7 and FIG. 8. FIG. 7 schematically illustrates a top view of a bio sensing device according to a third variant embodiment of the first embodiment of the present disclosure, and FIG. 8 schematically illustrates a sectional view of the bio sensing device according to a third variant embodiment of the first embodiment of the present disclosure. As shown in FIG. 7 and FIG. 8, in the bio sensing device 1*c* of this variant embodiment, a plurality of the light emitting elements 14 may be used to generate light of different wavelength bands respectively. In this case, one of the optical sensors 16 may, for example, include a plurality of photodiodes stacked with one another (e.g., including a photodiode 16*a*, a photodiode 16*b* and a photodiode 16*c* stacked in sequence) and used for detecting light of different wavelength bands respectively. In other words, a plurality of the light emitting elements 14 may correspond to one optical sensor 16. In the embodiment of FIG. 8, the photodiode 16*a*, the photodiode 16*b* and the photodiode 16*c* may be, for example, organic photodiodes, and the light emitting elements 14 may include a light emitting element 141*a*, a light emitting element 141*b*, and a light emitting element 141*c* that generate light of different wavelength bands respectively, in which the organic photodiodes stacked with each other may be used to respectively detect the light L1 generated by the light emitting element 141*a*, the light emitting element 141*b* and the light emitting element 141*c*, but not limited thereto. In some embodiments, optical sensor 16 may include a stacked structure of multiple organic semiconductor layers.

In the embodiment of FIG. 8, the position of the optical sensor 16 may use the structure of FIG. 6, and the optical sensor 16 may be located between the electrode E8 and the electrode E2, such that the distance T1 between the optical sensor 16 and the bottom surface of the medium layer 12 may be less than the distance T3 between the gate electrode G of the second transistor 20*b* and the medium layer 12, but not limited thereto. In some embodiments, the optical sensor 16 in FIG. 8 may use the configuration shown in FIG. 2 and be located on the electrode E2, but the present disclosure is not limited thereto.

In some embodiments, as shown in FIG. 8, the distance T2 between one of the light emitting elements 14 and the medium layer 12 may be less than the distance T4 between the gate electrode G of the first transistor 20*a* and the medium layer 12. For example, the light emitting element 14 may be at least partially overlapped with the first transistor 20*a* in a horizontal direction HD parallel to the upper surface 12S of the medium layer 12. For example, an upper surface of the light emitting element 14 may be located between an upper surface of the electrode E1 and a lower surface of the semiconductor layer SE in the horizontal direction HD, but not limited thereto. With this design, the number of insulating layers through which the light L1 moving from the light emitting element 14 to the skin layer 18 passes may be reduced, which reduces interference of the layers in the circuit layer 22 with the light L1 to improve the detection accuracy. For example, the light emitting element 14 may be attached to the upper surface 12S of the corresponding island portion 12P1 through the adhesive layer 34. In some embodiments, the adhesive layer 34 may have a transmittance greater than 80% with respect to the first wavelength light L1, but not limited thereto. When the optical sensor 16 and the light emitting element 14 are located in the circuit layer 22 in the horizontal direction HD, the bio sensing device 1*c* may not have the island structures 28 shown in FIG. 2 or FIG. 6, but not limited thereto. Other parts of the bio sensing device 1*c* in this variant embodiment may refer to the structures of the above-mentioned or following embodiments and are not redundantly detailed herein.

Figure 9:
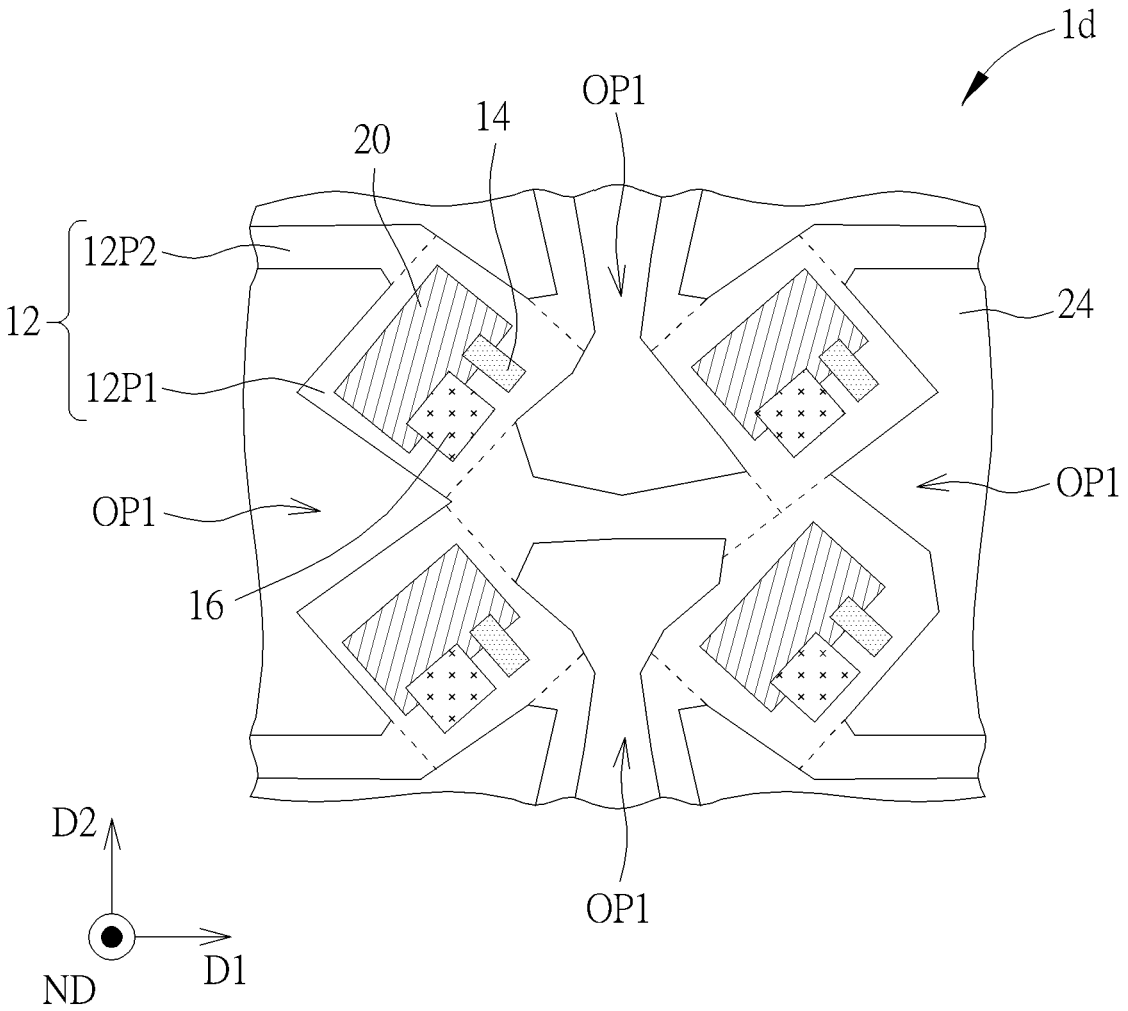
FIG. 9 schematically illustrates a top view of a bio sensing device according to a fourth variant embodiment of the first embodiment of the present disclosure.

Refer to FIG. 9, which schematically illustrates a top view of a bio sensing device according to a fourth variant embodiment of the first embodiment of the present disclosure. As shown in FIG. 9, in the bio sensing device 1*d* of this variant embodiment, one of the light emitting elements 14 and/or one of the optical sensors 16 may be overlapped with one of the transistor circuits 20 in the normal direction ND without affecting the detection of the bio sensing device 1*d* to the biological information, for example, without significantly affecting the path of light L1. By partially overlapping the transistor circuit 20 with the light emitting element 14 and/or the optical sensor 16, the transistor circuit 20 may for example include a greater number of transistors. As an example, the transistor circuit 20 may include six transistors and one capacitor or other structures, but not limited thereto. Other parts of the bio sensing device 1*d* in this variant embodiment may refer to the structures of the above-mentioned or following embodiments and are not detailed redundantly.

Figure 10:
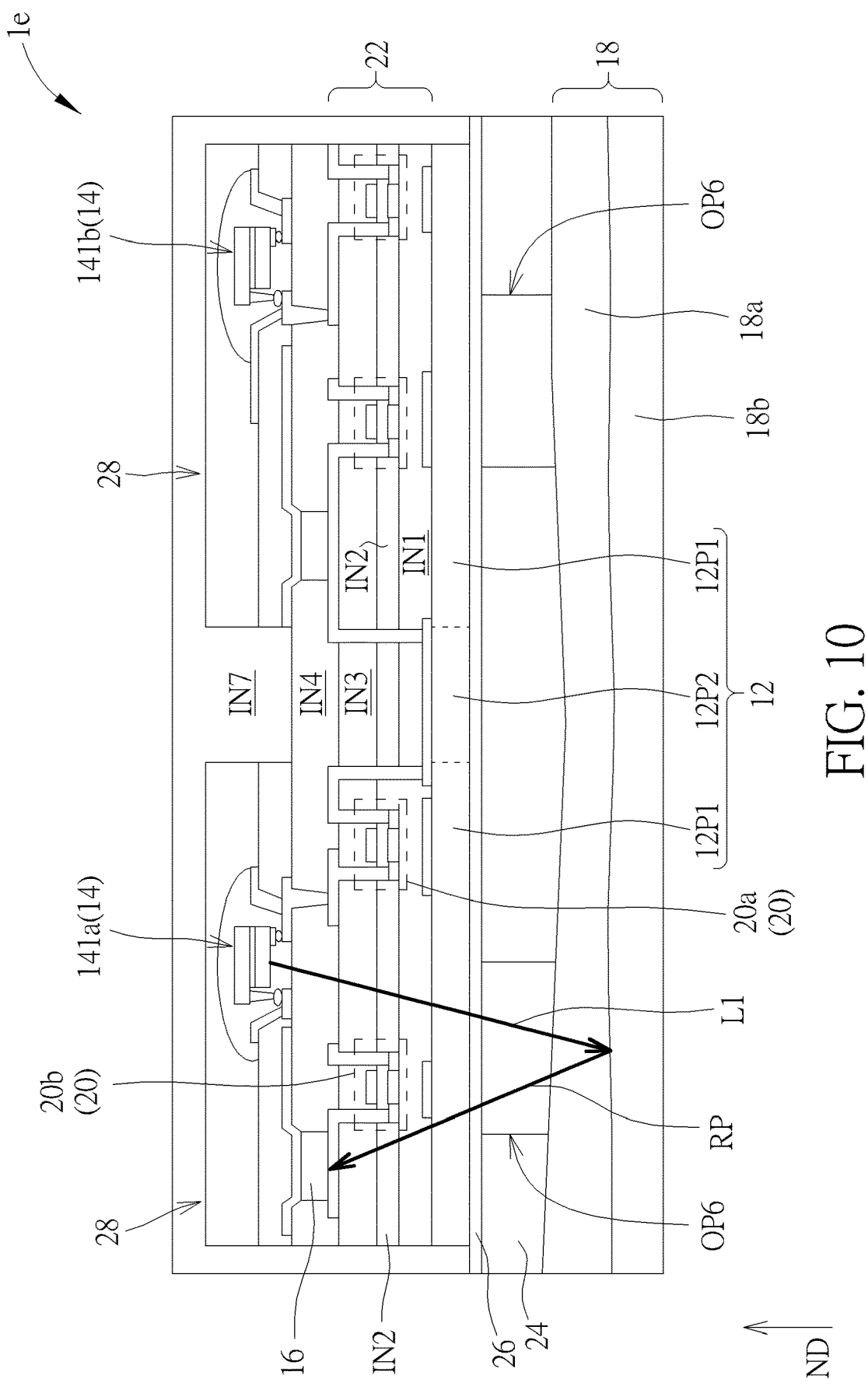
FIG. 10 schematically illustrates a sectional view of a bio sensing device according to a fifth variant embodiment of the first embodiment of the present disclosure.

Refer to FIG. 10, which schematically illustrates a sectional view of a bio sensing device according to a fifth variant embodiment of the first embodiment of the present disclosure. As shown in FIG. 10, in the biosensor 1*e* of this variant embodiment, the supporting layer 24 may have at least one opening OP6, and the opening OP6 may be overlapped with at least one of one of the light emitting elements 14 and one of the optical sensors 16 in the normal direction ND of the medium layer 12, such that the light L1 generated by the light emitting element 14 may enter the skin layer 18 through the opening OP6, and/or the reflected part RP reflected from the skin layer 18 may be directed to the optical sensor 16 through the same opening OP6, thereby improving detection accuracy. In some embodiments, the supporting layer 24 having the opening OP6 may include a transparent or opaque material, but not limited thereto.

In some embodiments, a transmittance of the circuit layer 22 and the insulating layer IN4 at one wavelength band may be less than another transmittance of the circuit layer 22 and the insulating layer IN4 at another wavelength band, in which the opening OP6 may correspond to the light emitting element 14 (e.g., one of the light emitting element 141*a* and the light emitting element 141*b*) that generates the light L1 corresponding to the wavelength band of less transmittance, and a part of the supporting layer 24 may not have the opening OP6 corresponding to the light emitting element 14 (e.g., the other one of the light emitting element 141*a* and the light emitting element 141*b*) that generates the light L1 corresponding to the wavelength band of greater transmittance, but the present disclosure is not limited thereto. In some embodiments, an extending direction of the opening OP6 may be, for example, parallel to a stretching direction of the bio sensing device 1*e*. Other parts of the bio sensing device 1*e* in this variant embodiment may refer to the structures of the above-mentioned or following embodiments and are not detailed redundantly.

Figure 11:
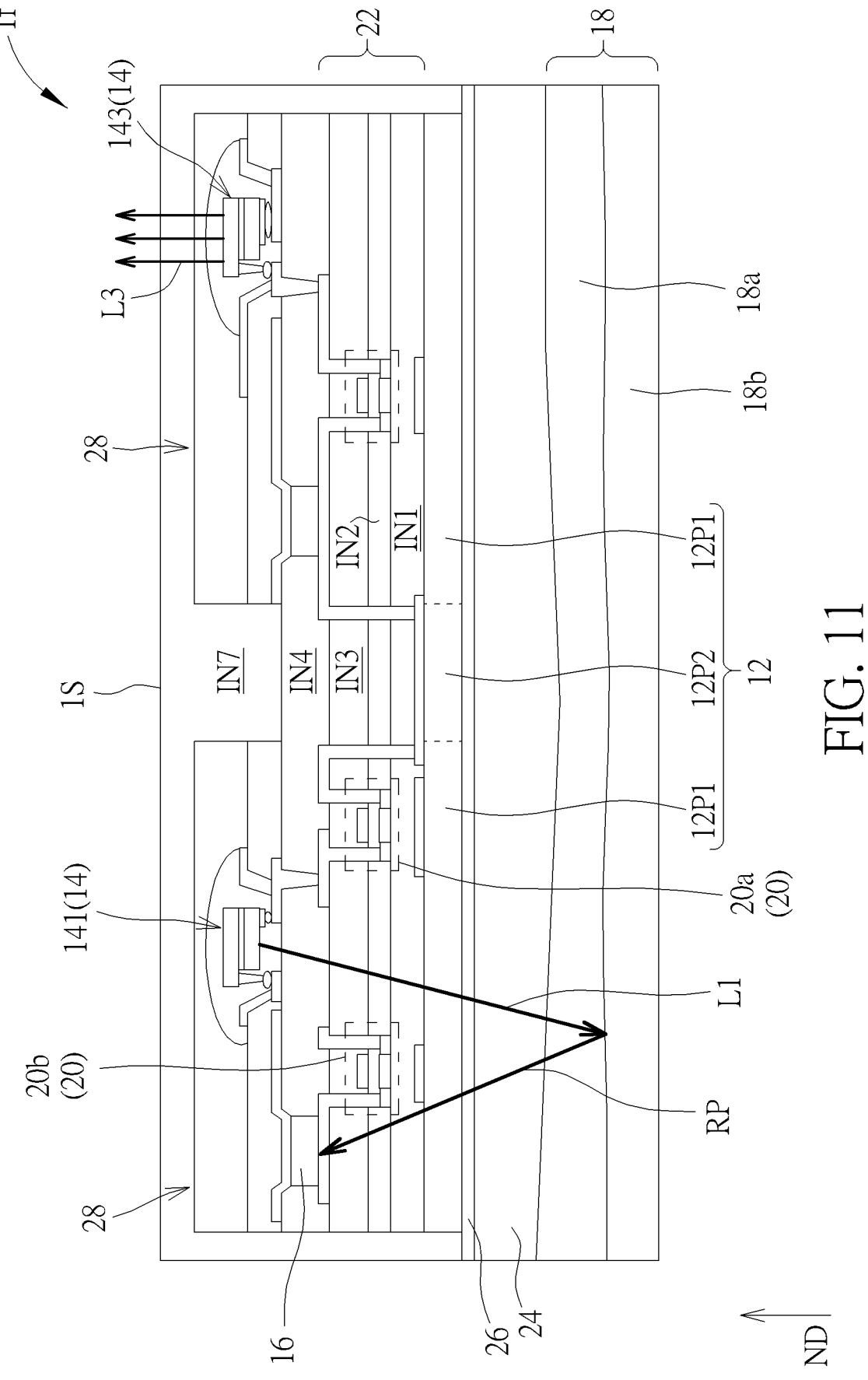
FIG. 11 schematically illustrates a sectional view of a bio sensing device according to a sixth variant embodiment of the first embodiment of the present disclosure.

Refer to FIG. 11, which schematically illustrates a sectional view of a bio sensing device according to a sixth variant embodiment of the first embodiment of the present disclosure. As shown in FIG. 11, in the bio sensing device if of this variant embodiment, the light emitting elements 14 may further include a third light emitting element 143 for generating light L3. Although FIG. 11 shows one third light emitting element 143, the number of the third light emitting element 143 of the present disclosure is not limited thereto and may be plural, for example. In the embodiment shown in FIG. 11, one of the first light emitting elements 141 for detecting the biological information and one of the third light emitting elements 143 for displaying images may be respectively disposed on different island portions 12P1, and the circuit layer 22 may further include a third transistor 20*c* directly connected to the third light emitting element 143 and used for controlling the third light emitting element 143, but not limited thereto. Through the installation of the third light emitting elements 143, the bio sensing device if may display images from its surface 1S opposite to the skin layer 18. Other parts of the bio sensing device if of this variant embodiment may refer to the structures of the above-mentioned or following embodiments and are not detailed redundantly.

Figure 12:
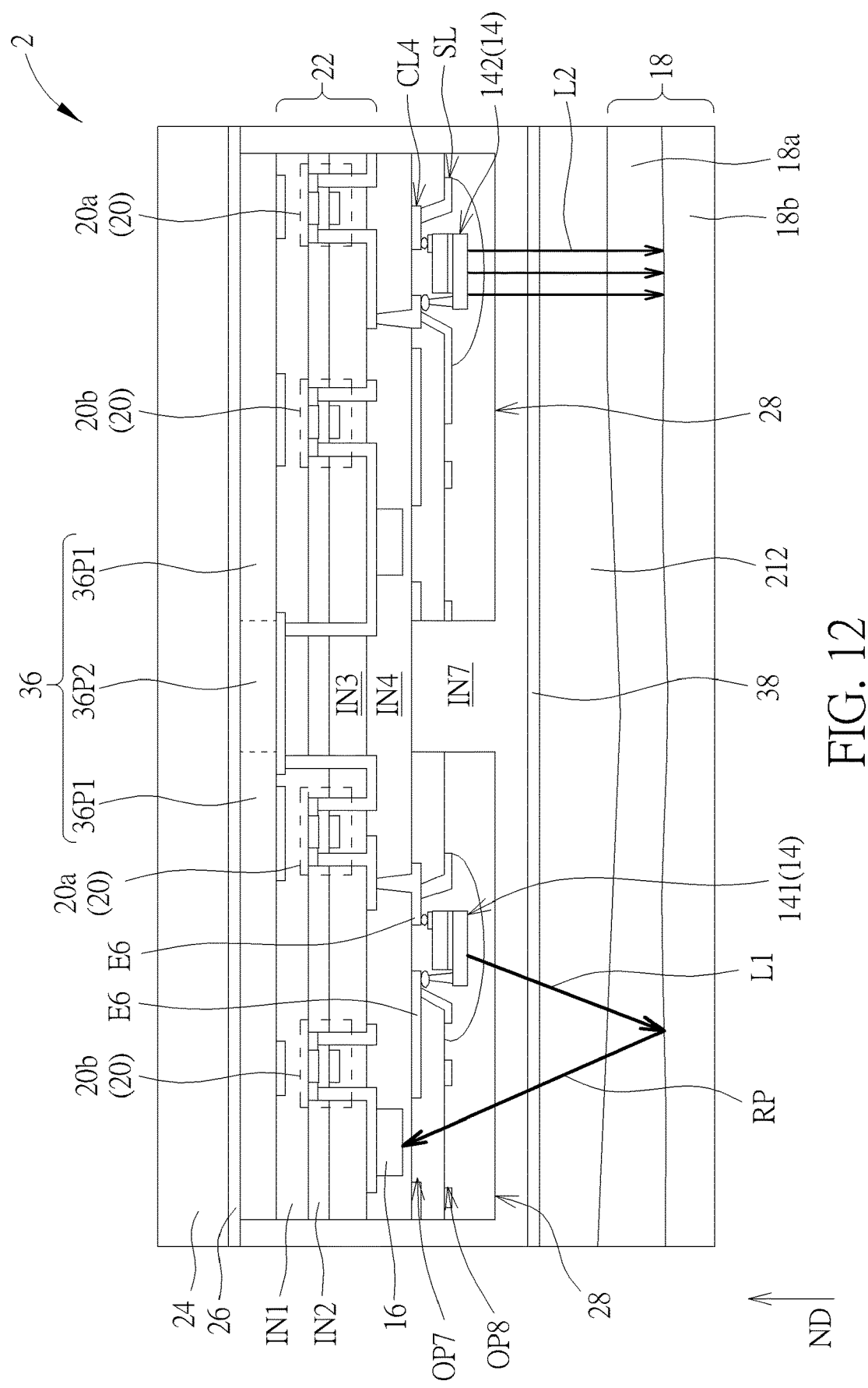
FIG. 12 schematically illustrates a sectional view of a bio sensing device according to a second embodiment of the present disclosure.

Refer to FIG. 12, which schematically illustrates a sectional view of a bio sensing device according to a second embodiment of the present disclosure. A top view of the bio sensing device 2 shown in FIG. 12 may refer to the content mentioned above, but not limited thereto. As shown in FIG. 12, the bio sensing device 2 of this embodiment differs from the bio sensing devices of the above-mentioned embodiments in that the light L1 generated by one of the light emitting elements 14 may be emitted from a side of the light emitting element 14 opposite to the circuit layer 22, and the medium layer 212 may be located between the light emitting elements 14 and the skin layer 18 and between the optical sensors 16 and the skin layer 18. It should be noted that the medium layer 212 of this embodiment may be different from the medium layer 12 of the above-mentioned embodiment.

Specifically, as shown in FIG. 12, the bio sensing device 2 may further include a base layer 36, wherein one of the light emitting elements 14 and one of the optical sensors 16 are disposed on the base layer 36 and disposed between the base layer 36 and the medium layer 12. In this embodiment, the base layer 36 may, for example, be the same as or similar to the medium layer 12 shown in FIG. 2 and may be, for example, a stretchable base layer. Also, the light emitting elements 14 and the optical sensors 16 may be formed on the base layer 36 through processes. In other words, the base layer 36 may be a substrate for disposing the light emitting elements 14 and the optical sensors 16. For example, a material of the base layer 36 may be the same as or similar to the material of the medium layer 12 in FIG. 2 and will not be repeated herein. In the embodiment of FIG. 12, the base layer 36 may be a patterned substrate, such that the base layer 36 may be stretchable, but not limited thereto. For example, the base layer 36 may also include a plurality of island portions 36P1 and at least one bridge portion 36P2, wherein the bridge portion 36P2 connects at least two of the island portions 36P1 to each other, and one of the light emitting elements 14 and one of the optical sensors 16 are disposed on at least one of the island portions 36P1. Since the island portion 36P1 and the bridge portion 36P2 may be respectively similar to or the same as the island portion 12P1 and the bridge portion 12P2 in FIG. 2, they are not detailed redundantly.

As shown in FIG. 12, the supporting layer 24 may be disposed on a side of the base layer 36 opposite to another side of the base layer 36 on which one of the light emitting elements 14 is disposed. Since the medium layer 212 may be disposed on a surface of the insulating layer IN7 opposite to the base layer 36 after the supporting layer 24 is disposed on the base layer 36, the medium layer 212 may use a material which has a tolerable temperature less than the process temperature for forming the circuit layer 22, the optical sensors 16, and the light emitting elements 14. For example, the material of the medium layer 212 may be similar to or the same as the material of the supporting layer 24. The material of the medium layer 212 may include, for example, PC, PMMA, acrylonitrile-butadiene-styrene copolymer (ABS) resin or other suitable materials. The medium layer 212 may be attached to the insulating layer IN7 through an adhesive layer 38, for example. In some embodiments, the adhesive layer 38 may have a transmittance greater than 80% at the first wavelength and/or the second wavelength, but not limited thereto.

In the embodiment of FIG. 12, the conductive layer CL4 may further have an opening OP7 overlapped with the optical sensor 16 in the normal direction ND to improve the collimation of the reflected part RP reflected from the skin layer 18. In some embodiments, the shielding layer SL may have an opening OP8 overlapped with the opening OP7 in the normal direction ND. A width of the opening OP8 may, for example, be greater than a width of the opening OP7, but not limited thereto. Other parts of the bio sensing device 2 of this embodiment refer to the structures of the above-mentioned or following embodiments and are not detailed redundantly.

It should be noted that since the light L1 of the light emitting elements 14 does not pass through the circuit layer 22, the position of the transistor circuits 20 in the normal direction does not need to consider affecting the path of the light L1, so that the design of the bio sensing device 2 of this embodiment may be easier. For example, the conductive layer CL3 is not limited to include the transparent conductive material and may include metal or other opaque conductive materials. Alternatively, the size of the opening between the electrodes E6 does not need to consider the intensity of the light L1 after passing through the opening. In some embodiments, one of the transistor circuits 20 may be overlapped with one of the light emitting elements 14 and/or one of the optical sensors 16 in the normal direction ND, but not limited thereto. In addition, since the light emitting element 14 and the optical sensor 16 may be interposed between the supporting layer 24 and the medium layer 212, moisture and oxygen may be blocked by the supporting layer 24 and the medium layer 212.

In some embodiments, one of the light emitting elements 14 may optionally emit another light toward the circuit layer 22 for indicating to the user (e.g., notifying the user that the detection is in progress). In this case, there may be an opening between the electrodes E6 corresponding to the light emitting element 14, or the electrodes E6 may include the transparent conductive material, but not limited thereto.

In some embodiments, the light emitting elements 14 of the bio sensing device 2 may further have the phototherapy function. For example, as shown in FIG. 12, the light emitting elements 14 may include a first light emitting element 141 for detecting biological information and a second light emitting element 142 for treating the skin layer 18 of the user, but not limited thereto. In some embodiments, the electrodes E6 may include the reflective conductive material to increase the intensity of the light L1 and/or the intensity of the light L2 emitted toward the skin layer 18.

Figure 13:
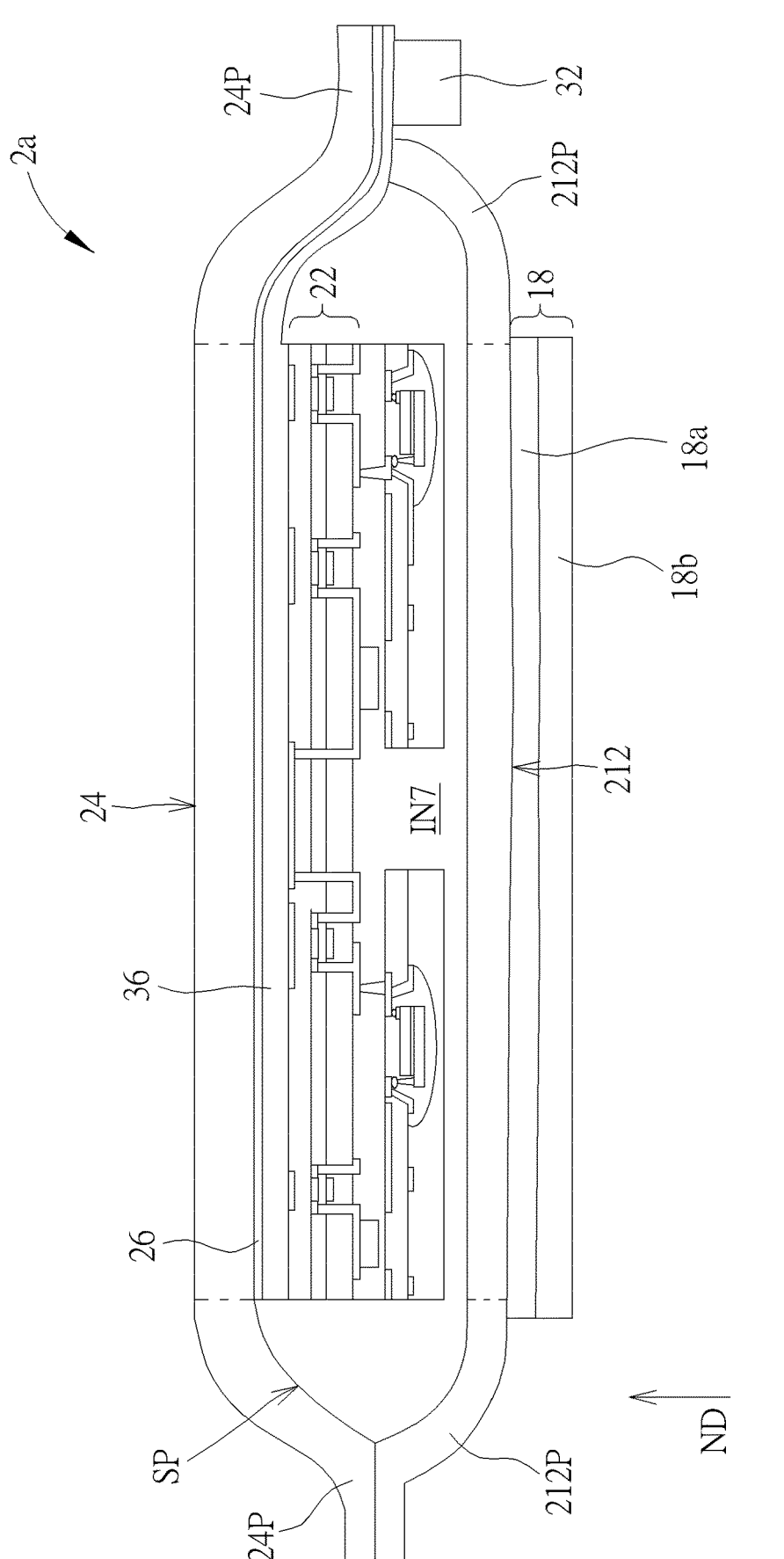
FIG. 13 schematically illustrates a sectional view of a bio sensing device according to a variant embodiment of the second embodiment of the present disclosure.

Refer to FIG. 13, which schematically illustrates a sectional view of a bio sensing device according to a variant embodiment of the second embodiment of the present disclosure. As shown in FIG. 13, in the bio sensing device 2a of this variant embodiment, the supporting layer 24 may be attached to at least a part of the medium layer 212, such that the supporting layer 24 and the medium layer 212 may form a sealed space SP, and the circuit layer 22, the light emitting elements 14 and the optical sensors 16 may be located in the sealed space SP. Accordingly, the effect of blocking moisture and oxygen may be improved. For example, the supporting layer 24 may have an edge portion 24P that is not overlapped with the circuit layer 22 in the normal direction ND, and the medium layer 212 may have an edge portion 212P that is not overlapped with the circuit layer 22 in the normal direction ND, in which the edge portion 24P may be attached to the edge portion 212P, but not limited thereto.

In some embodiments, the base layer 36 may extend to the edge portion 24P outside the sealed space SP, and the control element 32 may be disposed on the base layer 36 outside the sealed space SP, but not limited thereto. In this case, the circuit layer 22 may include traces (not shown) extending out of the sealed space SP along the base layer 36 to be coupled to the control element 32, but not limited thereto. In some embodiments, the supporting layer 24 may directly contact and be attached to the medium layer 212, such that the base layer 36 may be completely located in the sealed space SP, but not limited thereto. Other parts of the biosensor 2a of this variant embodiment may refer to the structures of the above-mentioned or the following embodiments and are not detailed redundantly.

Figure 14:
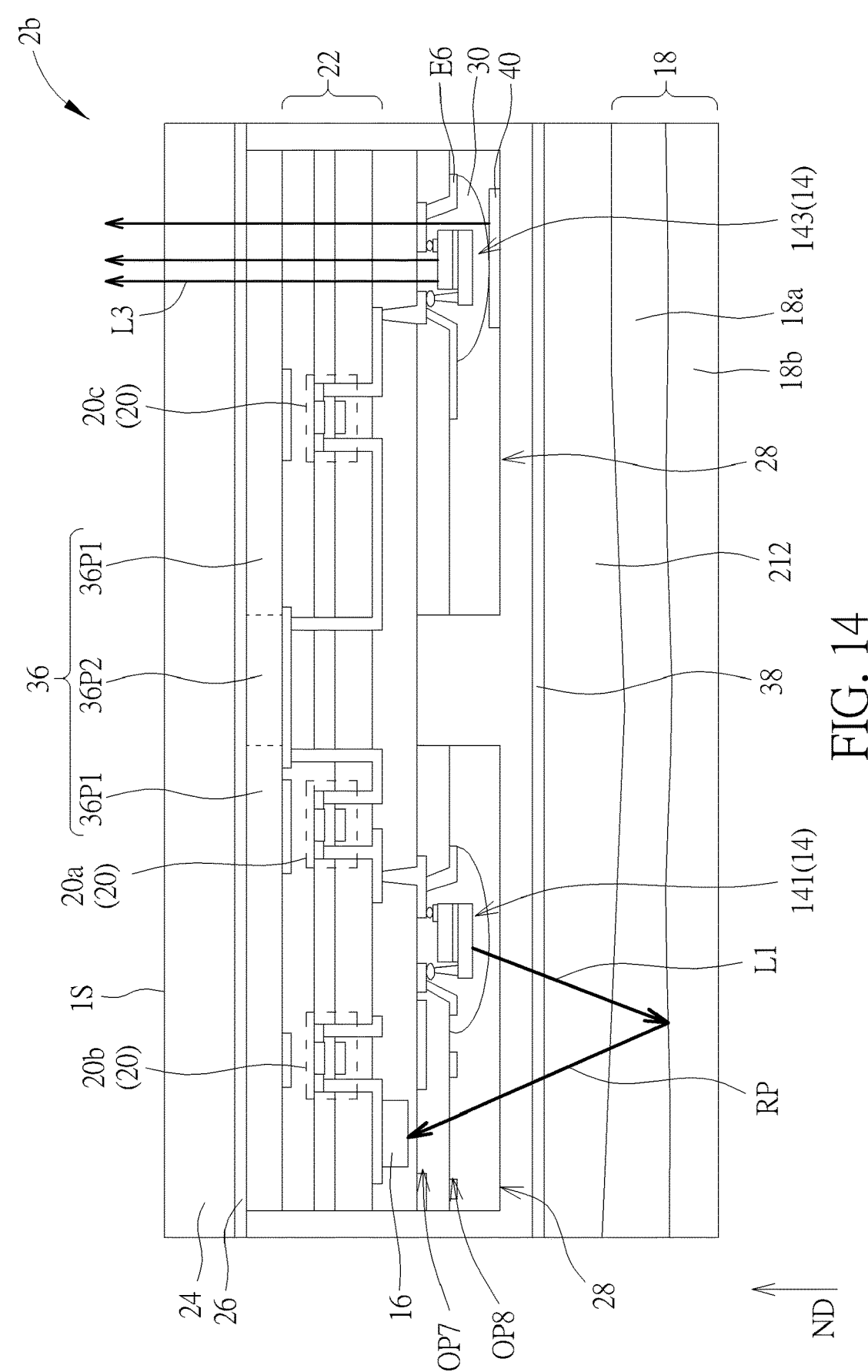
FIG. 14 schematically illustrates a sectional view of a bio sensing device according to another variant embodiment of the second embodiment of the present disclosure.

Refer to FIG. 14, which schematically illustrates a sectional view of a bio sensing device according to another variant embodiment of the second embodiment of the present disclosure. In the bio sensing device 2b of this variant embodiment, the light emitting elements 14 may further include a plurality of third light emitting elements 143 for generating light L3. In the embodiment shown in FIG. 14, one of the first light emitting elements 141 for detecting the biological information and one of the third light emitting elements 143 for displaying images may be respectively disposed on different island portions 12P1, and the circuit layer 22 may further include the third transistor 20c directly connected to the third light emitting element 143 and used for controlling the third light emitting element 143, but not limited thereto. Through the installation of the third light emitting elements 143, the bio sensing device 2b may display images from the surface 1S thereof opposite to the skin layer 18. In some embodiments, in order to increase the output of the light L3, there may be an opening between the electrodes E6 corresponding to the third light emitting element 143, or the electrodes E6 may include the transparent conductive material, but not limited thereto.

In the embodiment of FIG. 14, one of the island structures 28 corresponding to one of the third light emitting elements 143 may further include a reflective electrode 40 disposed on a side of the third light emitting element 143 facing the medium layer 212. The reflective electrode 40 may, for example, be disposed on a surface of the encapsulation layer 30 facing the medium layer 212 to reflect the light L3 generated by the third light emitting element 143, so as to increase the intensity of the light L3 emitted from the surface 1S of the bio sensing device 2b, but not limited thereto. Other parts of the bio sensing device 2b in this variant embodiment may refer to the structures of the above-mentioned or the following embodiments and are not detailed redundantly.

Figure 15:
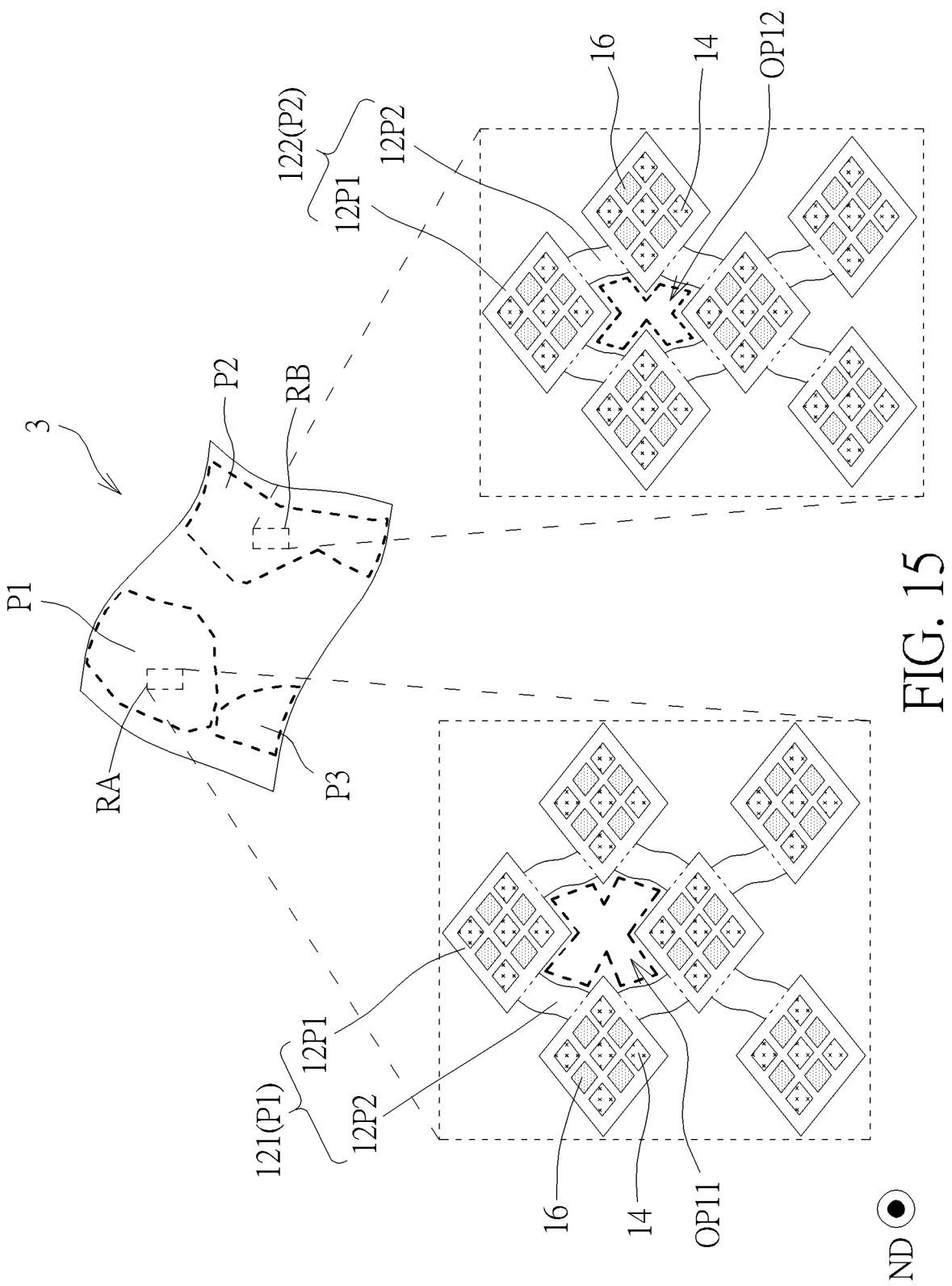
FIG. 15 schematically illustrates a top view of a bio sensing device according to a third embodiment of the present disclosure.

Refer to FIG. 15, which schematically illustrates a top view of a bio sensing device according to a third embodiment of the present disclosure, wherein a lower left portion and a lower right portion of FIG. 15 respectively show enlarged schematic views of a region RA and a region RB. As shown in FIG. 15, the bio sensing device 3 of this embodiment may include a first part P1, a second part P2 and a third part P3, which may be respectively used to be disposed on or attached to a surface with a first Gaussian curvature, a surface with a second Gaussian curvature and a surface with a third Gaussian curvature, and an absolute value of the first Gaussian curvature, an absolute value of the second Gaussian curvature and an absolute value of the third Gaussian curvature may be different from one another. Specifically, as shown in the lower left portion of FIG. 15, the medium layer 121 of the first part P1 may include a plurality of island portions 12P1 and a plurality of bridge portions 12P2, wherein one of the bridge portions 12P2 may connect two adjacent island portions 12P1 to each other, and the island portions 12P1 and the bridge portions 12P2 may surround a plurality of openings OP11. Similarly, as shown in the lower right portion of FIG. 15, the medium layer 122 of the second part P2 may include a plurality of island portions 12P1 and a plurality of bridge portions 12P2, wherein one of the bridge portions 12P2 may connect two adjacent island portions 12P1 to each other, and the island portions 12P1 and the bridge portions 12P2 may surround a plurality of openings OP12. It should be noted that an area of one of the openings OP11 may be greater than an area of one of the openings OP12, so that the stretchable degree of the first part P1 corresponding to the opening OP11 may be greater than that of the second part P2 corresponding to the opening OP12. Accordingly, the absolute value of the first Gaussian curvature may optionally be greater than the absolute value of the second Gaussian curvature. In this embodiment, the medium layer of the third part P3, for example, may not have the openings, so that a stretchable degree of the third part P3 may be less than that of the second part P2. The absolute value of the third Gaussian curvature may, for example, be less than the absolute value of the first Gaussian curvature and the absolute value of the second Gaussian curvature. For example, the absolute value of the third Gaussian curvature may be close to 0 or be 0, but not limited thereto. With the above design, the bio sensing device 3 may be disposed on or attached to a joint of biology or other biological features that need to be bent. In some embodiments, shapes of the openings OP11 and the openings OP12 may include, for example, X shapes, polygons or other suitable shapes, but not limited thereto. The medium layer 121 and the medium layer 122 of this embodiment may use the medium layer 12 shown in FIG. 2, but not limited thereto.

In the embodiment of FIG. 15, for example, a plurality of light emitting elements 14 and a plurality of optical sensors 16 may be disposed on each island portion 12P1 of the first part P1 and each island portion 12P1 of the second part P2. The light emitting elements 14 and the optical sensors 16 on the same one of the island portions 12P1 may be arranged in an array and in a staggered arrangement, but not limited thereto. In some embodiments, a top view structure of the first part P1 and/or a top view structure of the second part P2 may use any one of the top view structures shown in FIG. 1, FIG. 5, FIG. 7 and FIG. 9, but not limited thereto. In some embodiments, the relationship among positions of the light emitting elements 14, the optical sensors 16 and the island portions 12P1 of the first part P1 and/or the second part P2 may use the design of any of the above embodiments. In some embodiments, the medium layer 121 and the medium layer 122 in FIG. 15 may be any one of the medium layers 12 shown in FIG. 1 to FIG. 11 and the medium layers 212 shown in FIG. 12 to FIG. 14. Other parts of the bio sensing device 3 of this embodiment may refer to the structures of the above-mentioned embodiments and are not detailed redundantly. In some embodiments, the first part P1 and/or the second part P2 in FIG. 15 may be applied to any of the above-mentioned embodiments.

As mentioned above, in the bio sensing device of the present disclosure, since the medium layer has the first transmittance greater than 60% with respect to the first wavelength at which the light has the maximum intensity, the influence of the medium layer on the detection to the biological information may be reduced or avoided. Furthermore, by forming the optical sensors and light emitting elements on the stretchable medium layer or attaching the stretchable base layer formed with the optical sensors and light emitting elements to the medium layer, the bio sensing device may be stretchable. Accordingly, it is easy to repeatedly dispose or attach the bio sensing device to the skin layer while reducing damage to the elements. In addition, since the bio sensing device may be directly disposed or attached to the skin layer, the detection accuracy may be improved.

Those skilled in the art will readily observe that numerous modifications and alterations of the device and method may be made while retaining the teachings of the disclosure. Accordingly, the above disclosure should be construed as limited only by the metes and bounds of the appended claims.

What is claimed is:

1. A bio sensing device, comprising:

a medium layer;

a light emitting element configured to emit a light toward a user's skin layer, wherein the light passes through the medium layer and has a maximum intensity in a first wavelength;

an optical sensor configured to receive a reflected part of the light from the user's skin layer, wherein the reflected part of the light passes through the medium layer, and the light emitting element is not overlapped with the optical sensor in a normal direction of the medium layer; and a first transistor directly connected to the light emitting element, wherein a gate electrode of the first transistor is not overlapped with the light emitting element in the normal direction, wherein the medium layer has a first transmittance greater than 60% with respect to the first wavelength.

2. The bio sensing device according to claim 1, wherein the first transmittance is greater than 80%.

3. The bio sensing device according to claim 1, wherein the optical sensor has a maximum responsivity in a second wavelength, and the medium layer has a second transmittance greater than 60% with respect to the second wavelength.

4. The bio sensing device according to claim 3, wherein the second transmittance is greater than 80%.

5. The bio sensing device according to claim 1, further comprising a second transistor directly connected to the optical sensor, wherein a gate electrode of the second transistor is not overlapped with the optical sensor in the normal direction.

6. The bio sensing device according to claim 1, wherein a distance between the optical sensor and the medium layer is less than a distance between the light emitting element and the medium layer.

7. The bio sensing device according to claim 1, wherein a distance between the light emitting element and the medium layer is less than a distance between the gate electrode of the first transistor and the medium layer.

8. The bio sensing device according to claim 1, further comprising a second transistor directly connected to the optical sensor, wherein a distance between the optical sensor and the medium layer is less than a distance between a gate electrode of the second transistor and the medium layer.

9. The bio sensing device according to claim 1, wherein the medium layer is a stretchable medium layer.

10. The bio sensing device according to claim 9, wherein the medium layer comprises a plurality of island portions and a bridge portion connecting at least two of the plurality of island portions, and the light emitting element and the optical sensor are disposed on at least one of the plurality of island portions.

11. The bio sensing device according to claim 9, further comprising a supporting layer disposed under the medium layer, wherein the supporting layer comprises an opening overlapping at least one of the light emitting element and the optical sensor in the normal direction of the medium layer.

12. The bio sensing device according to claim 1, wherein the optical sensor comprises a plurality of photodiodes stacked with one another.

13. The bio sensing device according to claim 12, wherein the plurality of photodiodes are organic photodiodes.

14. The bio sensing device according to claim 1, wherein the light emitting element and the optical sensor are disposed on the medium layer.

15. The bio sensing device according to claim 1, further comprising a base layer, wherein the light emitting element and the optical sensor are disposed on the base layer and between the base layer and the medium layer.

16. The bio sensing device according to claim 15, wherein the base layer is a stretchable base layer.

17. The bio sensing device according to claim 16, wherein the base layer comprises a plurality of island portions and a bridge portion connecting at least two of the plurality of island portions, and the light emitting element and the optical sensor are disposed on at least one of the plurality of island portions.

18. The bio sensing device according to claim 16, further comprising a supporting layer disposed on a side of the base layer opposite to another side of the base layer on which the light emitting element is disposed.

*     *     *     *     *